(12) United States Patent
Harmer et al.

(10) Patent No.: US 12,207,915 B2
(45) Date of Patent: Jan. 28, 2025

(54) SYSTEMS AND METHODS FOR DETECTING MAGNETIC MARKERS FOR SURGICAL GUIDANCE

(71) Applicant: ENDOMAGNETICS LTD, Cambridge (GB)

(72) Inventors: Quentin John Harmer, Cambridge (GB); Tiziano Agostinelli, Cambridge (GB)

(73) Assignee: ENDOMAGNETICS LTD (GB)

(*) Notice: Subject to any disclaimer, the term of this patent is extended or adjusted under 35 U.S.C. 154(b) by 39 days.

(21) Appl. No.: 18/024,448

(22) PCT Filed: Sep. 6, 2021

(86) PCT No.: PCT/GB2021/052290
§ 371 (c)(1),
(2) Date: Mar. 2, 2023

(87) PCT Pub. No.: WO2022/049395
PCT Pub. Date: Mar. 10, 2022

(65) Prior Publication Data
US 2023/0277083 A1    Sep. 7, 2023

(30) Foreign Application Priority Data
Sep. 4, 2020   (GB) .................................... 2013909

(51) Int. Cl.
*A61B 5/06*   (2006.01)
*A61B 6/12*   (2006.01)
(Continued)

(52) U.S. Cl.
CPC ............... *A61B 5/062* (2013.01); *A61B 5/06* (2013.01); *A61B 34/20* (2016.02); *A61B 90/39* (2016.02);
(Continued)

(58) Field of Classification Search
CPC ... A61B 5/0205; A61B 5/7257; A61B 5/7267; A61B 5/7203; A61B 5/7264;
(Continued)

(56) References Cited

U.S. PATENT DOCUMENTS 5,079,006 A * 1/1992 Urquhart .............. A61K 9/5094
600/12
5,793,289 A   8/1998 Strzelec
(Continued)

OTHER PUBLICATIONS

PCT Inernational Search Report and PCT Written Opinion for PCT International Patent Application No. PCT/GB2021/052290; mailing date Nov. 15, 2021; (15 pages).
(Continued)

*Primary Examiner* — Keith M Raymond
*Assistant Examiner* — Johnathan Maynard
(74) *Attorney, Agent, or Firm* — K&L GATES

(57) ABSTRACT

Systems and Methods for Detecting Magnetic Markers for Surgical Guidance Methods and systems for detecting a magnetic marker for guiding a surgeon to a region of interest during a surgical procedure comprising generating a driving magnetic field having a cyclic pattern comprising two or more successive periods of time, the driving magnetic field having a substantially constant, non-zero amplitude during each of the successive periods of time, and the amplitude of the driving magnetic field during at least one of the periods of time being different from the amplitude of the driving magnetic field during at least one other of the periods of time; detecting a response magnetic field; selecting at least one signal from a plurality of sensed signals, each of which corresponds to the response magnetic field detected during a respective one of the successive periods of time of each cycle; determining a detection signal corresponding to the magnetic marker using the at least one selected signal; and
(Continued)

generating an output signal (e.g. an audio or display signal) based on a strength of the detection signal.

19 Claims, 7 Drawing Sheets

(51) Int. Cl.
*A61B 34/20* (2016.01)
*A61B 90/00* (2016.01)

(52) U.S. Cl.
CPC ......... *A61B 6/12* (2013.01); *A61B 2090/3954* (2016.02)

(58) Field of Classification Search
CPC . A61B 5/02405; A61B 5/742; A61B 5/02416; A61B 5/0816; A61B 5/4812; A61B 5/0059; A61B 5/4836; A61B 5/681; A61B 5/11; A61B 5/14551; A61B 2562/0219; A61B 5/7282; A61B 5/021; A61B 5/318; A61B 5/0031; A61B 5/024; A61B 5/0022; A61B 5/389; A61B 5/7275; A61B 5/055; A61B 5/369; A61B 5/4809; A61B 5/02438; A61B 5/4818; A61B 5/7278; A61B 2017/00084; A61B 5/374; A61B 8/485; A61B 5/0002; A61B 85/7221; A61B 5/0004; A61B 5/316; A61B 8/481; A61B 2018/00577; A61B 5/1118; A61B 2560/0223; A61B 5/00; A61B 5/05; A61B 5/7225; A61B 8/08; A61B 2018/00791; A61B 5/4094; A61B 5/4848; A61B 2090/378; A61B 8/5223; A61B 5/486; A61B 5/113; A61B 5/7239; A61B 5/4815; A61B 5/6824; A61B 85/01; A61B 5/4064; A61B 5/4839; A61B 2018/00875; A61B 5/1116; A61B 5/7246; A61B 5/746; A61B 5/6831; A61B 5/441; A61B 8/06; A61B 18/1206; A61B 5/02055; A61B 5/0507; A61B 5/0075; A61B 2017/00734; A61B 5/7207; A61B 5/02427; A61B 5/726; A61B 2560/0214; A61B 5/14546; A61B 5/0077; A61B 5/372; A61B 2017/320094; A61B 2018/00023; A61B 2090/374; A61B 2560/0219; A61B 5/1112; A61B 5/112; A61B 5/1123; A61B 5/6861; A61B 5/7285; A61B 5/7475; A61B 2017/320069; A61B 5/6802; A61B 2017/00477; A61B 2017/320095; A61B 2562/0247; A61B 5/0215; A61B 5/0533; A61B 5/165; A61B 5/4806; A61B 5/6844; A61B 7/003; A61B 2562/0271; A61B 8/0883; A61B 2017/00172; A61B 2018/00827; A61B 2560/0475; A61B 5/1455; A61B 5/398; A61B 5/6803; A61B 5/0245; A61B 5/24; A61B 5/6814; A61B 18/1445; A61B 2017/00398; A61B 2562/0238; A61B 5/0515; A61B 5/14539; A61B 5/7235; A61B 8/488; A61B 17/320068; A61B 2018/00601; A61B 2018/00994; A61B 5/4866; A61B 5/08; A61B 5/4833; A61B 8/461; A61B 8/5207; A61B 2562/16; A61B 5/02; A61B 5/6826; A61B 18/18; A61B 2017/00106; A61B 2017/0046; A61B 5/0066; A61B 5/291; A61B 5/4238; A61B 5/6804; A61B 8/14; A61B 17/320092; A61B 18/20; A61B 5/076; A61B 5/4035; A61B 8/00; A61B 8/483; A61B 2017/00017; A61B 2018/00892; A61B 5/073; A61B 5/117; A61B 5/7455; A61B 8/5269; A61B 5/0538; A61B 5/6852; A61B 5/7253; A61B 2017/00026; A61B 2018/00005; A61B 2034/2051; A61B 5/0024; A61B 5/7232; A61B 2017/00039; A61B 5/02007; A61B 5/0261; A61B 5/4082; A61B 8/54; A61B 18/14; A61B 2018/00607; A61B 5/062; A61B 5/087; A61B 5/16; A61B 5/352; A61B 5/38; A61B 5/411; A61B 5/6898; A61B 2017/00154; A61B 2090/065; A61B 2562/0223; A61B 2562/08; A61B 5/0006; A61B 5/0051; A61B 18/1815; A61B 2018/00589; A61B 2560/0443; A61B 34/20; A61B 5/015; A61B 5/725; A61B 7/04; A61B 8/0808; A61B 8/12; A61B 8/4416; A61B 2017/00123; A61B 2017/00876; A61B 2018/00452; A61B 2562/0204; A61B 2562/0233; A61B 5/0071; A61B 5/02125; A61B 5/1102; A61B 5/1126; A61B 5/14552; A61B 5/4821; A61B 18/1492; A61B 2017/00464; A61B 2562/0257; A61B 5/14542; A61B 5/201; A61B 5/415; A61B 5/6823; A61B 5/721; A61B 5/743; A61B 2090/064; A61B 5/0062; A61B 5/4029; A61B 5/6833; A61B 17/07207; A61B 2018/00446; A61B 2018/0063; A61B 2018/00904; A61B 2560/0242; A61B 34/30; A61B 5/1135; A61B 5/6829; A61B 2090/061; A61B 2562/12; A61B 2576/00; A61B 5/14532; A61B 5/375; A61B 7/00; A61B 8/085; A61B 2017/00199; A61B 2018/00702; A61B 2018/00785; A61B 2018/1876; A61B 5/053; A61B 5/377; A61B 8/4488; A61B 2017/00119; A61B 2017/320097; A61B 5/0082; A61B 5/02028; A61B 5/097; A61B 5/33; A61B 5/349; A61B 5/444; A61B 5/6832; A61B 90/98; A61B 17/22012; A61B 2017/00115; A61B 2017/0023; A61B 2017/00323; A61B 2018/00988; A61B 5/0255; A61B 5/1032; A61B 5/1121; A61B 5/7228; A61B 2018/1455; A61B 2560/0209; A61B 2562/227; A61B 5/0073; A61B 5/4047; A61B 5/4088; A61B 5/6801; A61B 5/684; A61B 2017/00022; A61B 2017/00402; A61B 5/002; A61B 5/02108; A61B 5/296; A61B 5/6813; A61B 8/13; A61B 8/56; A61B 90/90; A61B 17/225; A61B 2090/0803; A61B 2090/3966; A61B 5/0035; A61B 5/6822; A61B 2017/003; A61B 2017/00725; A61B 2562/046; A61B 5/02116; A61B 5/1114; A61B 5/128; A61B 8/0833; A61B 8/4483; A61B 18/04; A61B 18/042; A61B 2017/00075; A61B 2017/22008; A61B 2017/2929; A61B 2018/0019; A61B 2505/07; A61B 2505/09; A61B 5/4884; A61B 5/7217; A61B 1/00009; A61B 2017/00221; A61B 2017/00367; A61B 2018/00297; A61B 2018/00642; A61B 2217/005; A61B 2505/05; A61B 2562/0242; A61B 5/065; A61B 5/25; A61B 5/363; A61B 5/378; A61B 5/6821; A61B 8/04; A61B 8/5276; A61B 17/072; A61B 17/2258; A61B 18/12; A61B 2017/00482; A61B 2017/2927; A61B 2018/00494; A61B 2018/00779; A61B 2090/0811; A61B 2503/40; A61B 2562/164; A61B 5/0095; A61B 5/0295; A61B 5/037; A61B 5/0537; A61B 5/686; A61B 6/032; A61B 6/4035; A61B 8/4254; A61B 17/2202; A61B 2017/00473; A61B 2018/0016; A61B 2018/00767; A61B 34/70; A61B 5/02444; A61B 5/14556; A61B 5/339; A61B 5/361; A61B 5/6815; A61B 5/72; A61B 8/0891; A61B 8/463; A61B 8/52; A61B 1/041; A61B 18/1233; A61B 2018/00684; A61B 2018/126; A61B 2018/128; A61B 2503/10; A61B 2560/0204; A61B 34/35; A61B 5/0013; A61B 5/0036; A61B 5/0053; A61B 5/0823; A61B 5/1107; A61B 5/325; A61B 5/4041; A61B 6/548; A61B 17/068; A61B 18/203; A61B 2017/0069; A61B 2017/07271; A61B 2017/22014; A61B 2017/2923; A61B 2017/320074; A61B 2017/320078; A61B 2017/320089; A61B 2017/320093; A61B 2018/00678; A61B 2018/1226; A61B 2018/1861; A61B 2505/01; A61B 34/76; A61B 5/02158; A61B 5/03; A61B 5/031; A61B 5/0535; A61B 5/14507; A61B 5/332; A61B 5/4076; A61B 5/4211; A61B 5/6882; A61B 8/0816; A61B 8/0841; A61B 8/5261; A61B 90/37; A61B 17/1155; A61B 2017/2943; A61B 2017/320073; A61B 2018/00291; A61B 2018/00898; A61B 2217/007; A61B 2562/162; A61B 5/4803; A61B 5/687; A61B 6/484; A61B 6/583; A61B 8/4281; A61B 2017/0003; A61B 2017/00159; A61B 2017/00314; A61B 2018/00946; A61B 2034/101; A61B 2034/2063; A61B 2034/252; A61B 2034/742; A61B 2560/0468; A61B 2562/028; A61B 5/0015; A61B 5/0028; A61B 5/0042; A61B 5/0048; A61B 5/1113; A61B 5/1172; A61B 5/347; A61B 5/397; A61B 5/418; A61B 5/48; A61B 5/6817; A61B 5/6853; A61B 5/7271; A61B 5/74; A61B 1/00; A61B 18/1447; A61B 2017/00128; A61B 2017/00176; A61B 2017/22089; A61B 2017/320072; A61B 2018/00178; A61B 2018/00351; A61B 2018/00755; A61B 2018/2244; A61B 2090/3954; A61B 5/02141; A61B 5/277; A61B 5/407; A61B 5/42; A61B 5/4519; A61B 5/683; A61B 6/037; A61B 90/39; A61B 1/07; A61B 10/0012; A61B 17/22004; A61B 18/1402; A61B 2010/0019; A61B 2017/2903; A61B 2017/320071; A61B 2018/00011; A61B 2034/2072; A61B 2090/066; A61B 2090/376; A61B 2090/3929; A61B 2562/168; A61B 5/02255; A61B 5/028;

A61B 5/067; A61B 5/1072; A61B 5/145; A61B 5/30; A61B 5/346; A61B 5/4362; A61B 5/4842; A61B 5/4875; A61B 85/682; A61B 5/7242; A61B 50/13; A61B 6/4291; A61B 8/4427; A61B 8/466; A61B 8/469; A61B 1/00006; A61B 17/06166; A61B 17/32002; A61B 18/00; A61B 2017/00004; A61B 2017/07278; A61B 2018/00476; A61B 2018/00613; A61B 2018/124; A61B 2018/1823; A61B 2034/301; A61B 34/74; A61B 5/0026; A61B 5/0044; A61B 5/0803; A61B 5/1034; A61B 5/1101; A61B 5/1103; A61B 5/18; A61B 5/4557; A61B 5/6828; A61B 5/6876; A61B 5/7405; A61B 5/7435; A61B 8/4227; A61B 8/5246; A61B 8/546; A61B 1/00165; A61B 1/00172; A61B 1/042; A61B 1/05; A61B 17/58; A61B 18/085; A61B 18/26; A61B 2017/00137; A61B 2017/00327; A61B 2017/00393; A61B 2017/00694; A61B 2017/00973; A61B 2017/2925; A61B 5/7221; A61B 2018/00619; A61B 2018/00714; A61B 2018/266; A61B 2034/2048; A61B 2090/031; A61B 2090/033; A61B 2090/034; A61B 2560/0228; A61B 5/06; A61B 5/0826; A61B 5/1176; A61B 5/245; A61B 5/287; A61B 5/355; A61B 5/366; A61B 5/4824; A61B 5/6896; A61B 6/405; A61B 6/466; A61B 6/5205; A61B 6/5258; A61B 6/5282; A61B 8/467; A61B 8/565; A61B 17/00234; A61B 17/2256; A61B 17/29; A61B 2017/07285; A61B 2018/1253; A61B 2018/2205; A61B 2018/2261; A61B 2034/102; A61B 2090/0808; A61B 2090/0809; A61B 2560/0276; A61B 2562/02; A61B 2562/04; A61B 2576/026; A61B 3/113; A61B 5/0068; A61B 5/085; A61B 5/0871; A61B 5/163; A61B 5/344; A61B 5/6866; A61B 5/6868; A61B 6/00; A61B 8/4444; A61B 8/543; A61B 90/00; A61B 17/1285; A61B 18/082; A61B 2017/22088; A61B 2017/2901; A61B 2018/00273; A61B 2018/00303; A61B 2018/00797; A61B 2018/00839; A61B 2018/0091; A61B 2090/062; A61B 2560/0247; A61B 5/0008; A61B 5/0064; A61B 5/02152; A61B 5/026; A61B 5/0531; A61B 5/0809; A61B 5/308; A61B 5/35; A61B 5/36; A61B 5/383; A61B 5/4058; A61B 5/70; A61B 6/504; A61B 8/02; A61B 8/44; A61B 8/48; A61B 90/36; A61B 90/50; A61B 17/0057; A61B 17/0467; A61B 17/0469; A61B 17/12013; A61B 17/32056; A61B 18/02; A61B 18/1477; A61B 2017/00358; A61B 2017/22024; A61B 2017/22028; A61B 2018/00321; A61B 2018/00666; A61B 2018/00708; A61B 2034/305; A61B 2090/0807; A61B 2090/309; A61B 2090/3762; A61B 2503/42; A61B 2560/04; A61B 2562/0285; A61B 34/25; A61B 34/37; A61B 34/77; A61B 5/0046; A61B 5/0285; A61B 5/029; A61B

5/1104; A61B 5/1106; A61B 5/1117;
A61B 5/14553; A61B 5/168; A61B
5/282; A61B 5/293; A61B 5/341; A61B
5/367; A61B 5/395; A61B 5/4523; A61B
5/4528; A61B 5/4533; A61B 5/4857;
A61B 5/6812; A61B 5/6816; A61B
5/6869; A61B 5/6891; A61B 6/507; A61B
8/0858; A61B 8/4218; A61B 8/4263;
A61B 8/58; A61B 1/00004; A61B 1/045;
A61B 17/295; A61B 2017/0038; A61B
2017/00389; A61B 2017/00411; A61B
2017/00415; A61B 2017/00809; A61B
2017/1205; A61B 2017/22001; A61B
2017/2932; A61B 2017/320098; A61B
2018/00357; A61B 2018/00404; A61B
2018/00625; A61B 2018/00982; A61B
2018/144; A61B 2018/1452; A61B
2018/1465; A61B 2034/104; A61B
2034/2059; A61B 2050/301; A61B
2090/0481; A61B 2090/365; A61B
2090/397; A61B 2503/045; A61B
2560/02; A61B 2560/0252; A61B
2560/0257; A61B 2560/045; A61B
2562/182; A61B 2576/023; A61B 3/14;
A61B 3/145; A61B 5/0079; A61B
5/02133; A61B 5/064; A61B 5/091; A61B
5/1076; A61B 5/121; A61B 5/14535;
A61B 5/1459; A61B 5/246; A61B 5/384;
A61B 5/388; A61B 5/4205; A61B
5/6877; A61B 5/7425; A61B 5/7445;
A61B 50/20; A61B 6/481; A61B 8/145;
A61B 8/4209; A61B 8/4405; A61B
8/4466; A61B 8/4477; A61B 8/4494;
A61B 8/486; A61B 1/000094; A61B
1/233; A61B 1/2676; A61B 1/2736; A61B
1/31; A61B 1/313; A61B 10/007; A61B
17/00491; A61B 17/0206; A61B 17/115;
A61B 17/3468; A61B 2017/00061; A61B
2017/00092; A61B 2017/00146; A61B
2017/00203; A61B 2017/00216; A61B
2017/22009; A61B 2017/22015; A61B
2017/2904; A61B 2017/2916; A61B
2017/2936; A61B 2018/0053; A61B
2018/0047; A61B 2018/00636; A61B
2018/0066; A61B 2018/00886; A61B
2018/00922; A61B 2018/0094; A61B
2018/0212; A61B 2018/0293; A61B
2034/105; A61B 2090/3612; A61B
2090/373; A61B 2090/502; A61B
2218/002; A61B 2503/04; A61B 2503/22;
A61B 2560/0266; A61B 2560/0412;
A61B 2562/18; A61B 2562/223; A61B
2576/02; A61B 3/0025; A61B 3/10; A61B
5/0275; A61B 5/0836; A61B 5/12; A61B
5/243; A61B 5/28; A61B 5/413; A61B
5/4872; A61B 5/6805; A61B 5/7465;
A61B 5/7485; A61B 6/04; A61B 6/482;
A61B 6/503; A61B 8/0875; A61B
8/4245; A61B 90/10; A61B 10/0038;
A61B 10/0051; A61B 17/12118; A61B
17/12181; A61B 2010/0029; A61B
2010/0077; A61B 2017/00185; A61B
2017/00243; A61B 2017/0065; A61B
2017/00867; A61B 2017/22039; A61B
2018/00041; A61B 2018/00196; A61B
2018/00648; A61B 2018/00726; A61B
2018/00761; A61B 2018/1475; A61B
2018/1807; A61B 2018/20357; A61B
2018/208; A61B 2090/3908; A61B
2218/006; A61B 2503/12; A61B 2505/03;
A61B 2560/0261; A61B 2560/0462;
A61B 2562/043; A61B 5/0037; A61B
5/004; A61B 5/0093; A61B 5/02216;
A61B 5/0833; A61B 5/103; A61B 5/15;
A61B 5/205; A61B 5/222; A61B 5/256;
A61B 5/294; A61B 5/311; A61B 5/313;
A61B 5/343; A61B 5/37; A61B 5/392;
A61B 5/4023; A61B 5/41; A61B 5/416;
A61B 5/4255; A61B 5/4863; A61B
5/4869; A61B 5/489; A61B 5/6806; A61B
5/6825; A61B 5/6846; A61B 5/6887;
A61B 5/7214; A61B 5/7415; A61B
5/744; A61B 6/40; A61B 6/4417; A61B
6/5264; A61B 6/54; A61B 8/0825; A61B
8/445; A61B 8/5292; A61B 90/11; A61B
90/361; A61B 1/00121; A61B 1/00124;
A61B 1/00149; A61B 1/0016; A61B
1/018; A61B 10/00; A61B 17/12022;
A61B 17/2251; A61B 2017/00318; A61B
2017/00769; A61B 2017/00845; A61B
2017/00982; A61B 2017/22062; A61B
2017/320008; A61B 2017/32007; A61B
2017/320084; A61B 2018/0072; A61B
2018/00732; A61B 2018/1273; A61B
2018/1435; A61B 2034/2053; A61B
2034/2065; A61B 2034/306; A61B
2034/731; A61B 2090/0463; A61B
2090/063; A61B 2090/3616; A61B
2090/3782; A61B 2090/3904; A61B
2090/3925; A61B 2090/3987; A61B
2562/0209; A61B 2562/146; A61B
2562/166; A61B 2562/185; A61B 3/16;
A61B 5/0017; A61B 5/0084; A61B
5/02233; A61B 5/063; A61B 5/0876;
A61B 5/1124; A61B 5/227; A61B 5/242;
A61B 5/259; A61B 5/279; A61B 5/288;
A61B 5/333; A61B 5/381; A61B 5/40;
A61B 5/417; A61B 5/4561; A61B 5/483;
A61B 5/6838; A61B 5/6843; A61B
5/6862; A61B 5/6886; A61B 6/03; A61B
6/12; A61B 6/4007; A61B 6/4064; A61B
6/4258; A61B 8/429; A61B 8/4411; A61B
8/587; A61B 1/00013; A61B 1/00045;
A61B 1/00071; A61B 1/0057; A61B
1/051; A61B 1/303; A61B 10/02; A61B
17/00; A61B 17/0401; A61B 17/12031;
A61B 17/12122; A61B 17/12172; A61B
17/12177; A61B 17/24; A61B 17/3203;
A61B 17/42; A61B 18/1485; A61B
18/16; A61B 18/22; A61B 18/24; A61B
2017/00053; A61B 2017/00057; A61B
2017/00132; A61B 2017/0019; A61B
2017/00212; A61B 2017/00486; A61B
2017/00526; A61B 2017/00575; A61B
2017/00964; A61B 2017/22027; A61B
2017/22038; A61B 2017/22051; A61B
2017/22054; A61B 2017/22081; A61B
2017/22082; A61B 2017/22094; A61B
2017/2931; A61B 2017/2933; A61B
2017/2934; A61B 2017/925; A61B

2017/928; A61B 2018/00202; A61B 2018/0022; A61B 2018/00267; A61B 2018/00315; A61B 2018/005; A61B 2018/00571; A61B 2018/00595; A61B 2018/00803; A61B 2018/00821; A61B 2018/0262; A61B 2018/1286; A61B 2018/1425; A61B 2018/1472; A61B 2018/20359; A61B 2034/302; A61B 2090/067; A61B 2090/306; A61B 2090/3784; A61B 2090/3958; A61B 2090/3983; A61B 2090/3995; A61B 2218/007; A61B 2503/02; A61B 2560/0431; A61B 2562/0261; A61B 3/0041; A61B 3/1233; A61B 34/10; A61B 34/71; A61B 5/0033; A61B 5/0086; A61B 5/022; A61B 5/02225; A61B 5/0263; A61B 5/0522; A61B 5/0536; A61B 5/068; A61B 5/082; A61B 5/1122; A61B 5/1128; A61B 5/125; A61B 5/14514; A61B 5/1486; A61B 5/150007; A61B 5/150809; A61B 5/150816; A61B 5/150824; A61B 5/167; A61B 5/283; A61B 5/322; A61B 5/412; A61B 5/4244; A61B 5/4312; A61B 5/4845; A61B 5/4851; A61B 5/4854; A61B 5/6807; A61B 5/6848; A61B 5/6884; A61B 5/6892; A61B 5/7289; A61B 5/7292; A61B 5/748; A61B 6/0435; A61B 6/06; A61B 6/4233; A61B 6/4411; A61B 6/487; A61B 6/50; A61B 6/502; A61B 6/508; A61B 6/5247; A61B 6/527; A61B 6/5288; A61B 8/0866; A61B 8/4272; A61B 90/06; A61B 90/20; A61B 90/30; A61M 2205/50; A61M 2205/52; A61M 21/02; A61M 2205/8206; A61M 2021/0027; A61M 2205/3592; A61M 11/005; A61M 2205/505; A61M 2205/3375; A61M 2205/3331; A61M 15/0085; A61M 15/06; A61M 2205/0294; A61M 2205/3368; A61M 2205/6018; A61M 2205/587; A61M 2205/581; A61M 2016/0027; A61M 2205/60; A61M 15/0021; A61M 2016/0024; A61M 2205/3569; A61M 2205/8237; A61M 2205/18; A61M 2205/502; A61M 2021/0044; A61M 37/0092; A61M 5/14248; A61M 2021/0022; A61M 2205/583; A61M 2230/10; A61M 2205/3553; A61M 2205/276; A61M 21/00; A61M 2205/3317; A61M 2205/3306; A61M 2016/0033; A61M 2021/0055; A61M 2021/0072; A61M 2205/0266; A61M 2209/086; A61M 1/74; A61M 15/0066; A61M 2005/14268; A61M 2205/584; A61M 2205/8212; A61M 5/14224; A61M 15/008; A61M 2205/15; A61M 2205/42; A61M 2205/70; A61M 2230/63; A61M 1/73; A61M 1/732; A61M 1/743; A61M 15/0083; A61M 2021/005; A61M 2205/3584; A61M 1/962; A61M 2205/7536; A61M 1/96; A61M 1/982; A61M 1/82; A61M 1/86; A61M 1/982; A61M 1/985; A61M 2016/0021; A61M 2205/0272; A61M 2205/6027; A61M 2207/00; A61M 15/0081; A61M 2230/06; A61M 2202/0468; A61M 2205/3334; A61M 5/14244; A61M 39/08; A61M 2230/40; A61M 39/1011; A61M 2230/42; A61M 2205/273; A61M 2205/3576; A61M 2021/0083; A61M 39/12; A61M 2205/121; A61M 2205/123; A61M 16/0051; A61M 5/1782; A61M 2205/332; A61M 2202/0208; A61M 2230/50; A61M 2205/0205; A61M 2230/005; A61M 2230/04; A61M 2230/65; A61M 2205/8262; A61M 2230/30; A61M 2230/60; A61M 15/025; A61M 2021/0016; A61M 2205/609; A61M 2209/01; A61M 5/16831; A61M 60/148; A61M 60/178; A61M 16/0072; A61M 2039/009; A61M 2210/0612; A61M 5/1684; A61M 16/16; A61M 16/0069; A61M 2205/21; A61M 15/0003; A61M 16/026; A61M 16/0683; A61M 2005/14208; A61M 2039/0244; A61M 2205/0211; A61M 2205/3389; A61M 2205/6009; A61M 2205/702; A61M 15/0048; A61M 2005/1587; A61M 2205/507; A61M 5/14216; A61M 5/158; A61M 5/16881; A61M 5/172; A61M 5/36; A61M 15/001; A61M 15/002; A61M 16/024; A61M 2205/3303; A61M 2209/088; A61M 5/142; A61M 60/279; A61M 1/80; A61M 2206/22; A61M 2209/045; A61M 5/14586; A61M 5/16809; A61M 16/06; A61M 2005/1585; A61M 2005/1586; A61M 2025/1054; A61M 2039/1027; A61M 2230/14; A61M 2230/205; A61M 5/162; A61M 60/419; A61M 60/585; A61M 2021/0077; A61M 2205/8243; A61M 2230/08; A61M 15/009; A61M 16/00; A61M 2037/0007; A61M 2205/43; A61M 2205/582; A61M 31/00; A61M 1/36224; A61M 1/36225; A61M 1/3639; A61M 2021/0066; A61M 2205/3313; A61M 2205/3327; A61M 2205/3358; A61M 2210/0693; A61M 39/0208; A61M 5/14276; A61M 5/16886; A61M 5/1723; A61M 11/00; A61M 2021/0033; A61M 2205/057; A61M 2205/36; A61M 2205/3673; A61M 2209/084; A61M 2210/0625; A61M 60/422; A61M 60/546; A61M 1/3656; A61M 16/0633; A61M 2205/0238; A61M 2205/054; A61M 2205/3561; A61M 60/232; A61M 60/816; A61M 1/154; A61M 1/155; A61M 11/042; A61M 16/107; A61M 2021/0038; A61M 2205/05; A61M 2205/3546; A61M 2206/14; A61M 2206/16; A61M 5/3145; A61M 5/445; A61M 60/237; A61M 60/538; A61M 60/806; A61M 60/875; A61M 1/156; A61M 1/1565; A61M 1/1609; A61M 1/166; A61M 1/1692; A61M 1/1696; A61M 1/3621; A61M 1/36226; A61M 1/362265; A61M 1/367; A61M 1/77; A61M 16/0006; A61M 2039/0036; A61M 2202/07; A61M 2205/04; A61M 2205/3324; A61M 2205/3386; A61M 2205/3393; A61M

2205/7545; A61M 2209/082; A61M 27/006; A61M 39/10; A61M 5/16877; A61M 60/113; A61M 60/20; A61M 60/37; A61M 60/405; A61M 60/508; A61M 60/873; A61M 60/876; A61M 1/025; A61M 1/0281; A61M 1/14; A61M 1/152; A61M 1/16; A61M 1/1607; A61M 1/3437; A61M 1/36222; A61M 1/3623; A61M 1/60; A61M 1/63; A61M 1/631; A61M 1/71; A61M 1/72; A61M 1/742; A61M 1/78; A61M 1/782; A61M 1/784; A61M 1/79; A61M 15/0086; A61M 16/0003; A61M 16/0063; A61M 16/101; A61M 16/161; A61M 2016/1025; A61M 2021/0088; A61M 2202/0415; A61M 2205/051; A61M 2205/052; A61M 2205/12; A61M 2205/125; A61M 2205/17; A61M 2205/3355; A61M 2205/35; A61M 2205/3653; A61M 2205/707; A61M 2205/75; A61M 2205/7563; A61M 2230/20; A61M 2230/62; A61M 3/0201; A61M 5/007; A61M 5/1415; A61M 5/14232; A61M 16/0666; A61M 16/0677; A61M 16/1005; A61M 16/105; A61M 2005/16863; A61M 2016/0039; A61M 2039/1061; A61M 2202/0007; A61M 2205/0216; A61M 2205/058; A61M 2205/07; A61M 2205/106; A61M 2205/13; A61M 2205/3365; A61M 2205/3515; A61M 2205/3606; A61M 2205/362; A61M 2205/80; A61M 2205/825; A61M 2210/06; A61M 2210/0662; A61M 2210/0687; A61M 2230/18; A61M 35/00; A61M 35/003; A61M 5/31528; A61M 5/31551; A61M 5/31568; A61M 5/31585; A61M 5/31593; A61M 1/1524; A61M 15/00; A61M 16/0096; A61M 16/021; A61M 16/047; A61M 16/0672; A61M 16/12; A61M 16/209; A61M 2005/31588; A61M 2021/0005; A61M 2025/0002; A61M 2039/1016; A61M 2202/30; A61M 2205/0233; A61M 2205/3344; A61M 2205/3633; A61M 2205/6054; A61M 2230/432; A61M 2240/00; A61M 25/0009; A61M 25/0012; A61M 25/0116; A61M 25/04; A61M 25/10184; A61M 25/104; A61M 3/02; A61M 31/002; A61M 37/00; A61M 5/14546; A61M 5/14566; A61M 5/20; A61M 5/44; A61M 60/196; A61M 60/216; A61M 60/515; A61M 60/531; A61M 60/569

See application file for complete search history.

(56) References Cited

U.S. PATENT DOCUMENTS

| | | | |
|---|---|---|---|
| 6,230,038 B1* | 5/2001 | von Gutfeld | A61N 5/1049 600/409 |
| 6,337,627 B1* | 1/2002 | Von Gutfeld | A61B 5/06 324/326 |
| 2003/0006759 A1* | 1/2003 | Govari | A61B 5/06 324/207.13 |
| 2003/0036695 A1* | 2/2003 | Govari | A61B 5/065 324/207.13 |
| 2003/0040670 A1* | 2/2003 | Govari | A61B 5/062 324/207.13 |
| 2014/0266175 A1* | 9/2014 | Hattersley | A61B 5/05 324/243 |
| 2016/0124057 A1* | 5/2016 | Hattersley | G01R 33/1276 324/234 |
| 2019/0029560 A1 | 1/2019 | Harmer et al. | |
| 2019/0223975 A1* | 7/2019 | Agostinelli | A61B 90/39 |

OTHER PUBLICATIONS

Waanders, S. et al.; "A handheld SPIO-based sentinel lymph node mapping device using differential magnetometry"; Institute of Physics and Engineering in Medicine; vol. 61; (2016); pp. 8120-8134.

* cited by examiner

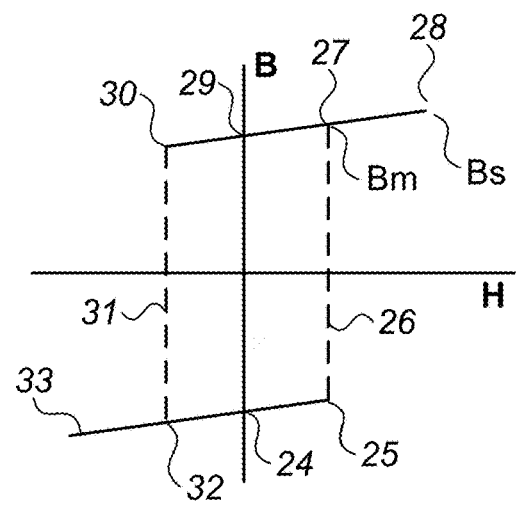
FIG. 5A
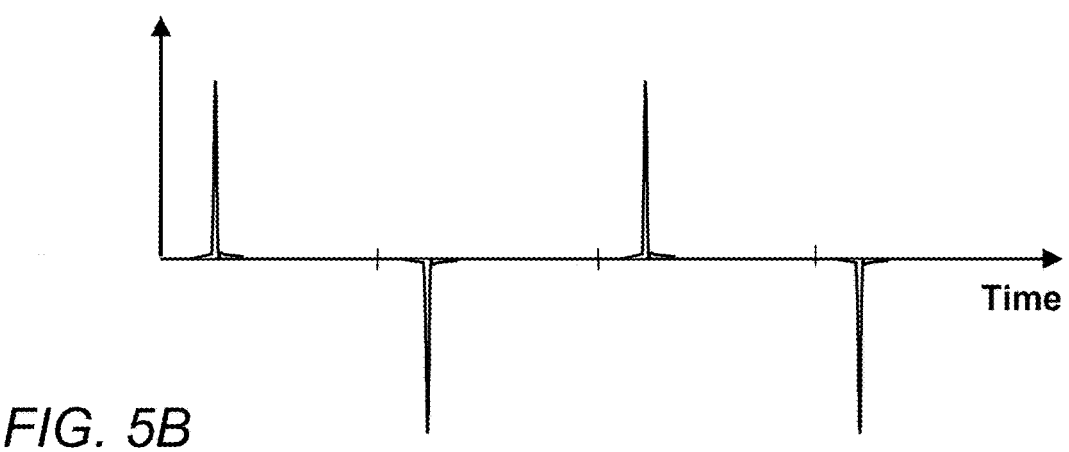
FIG. 5B
FIG. 5C
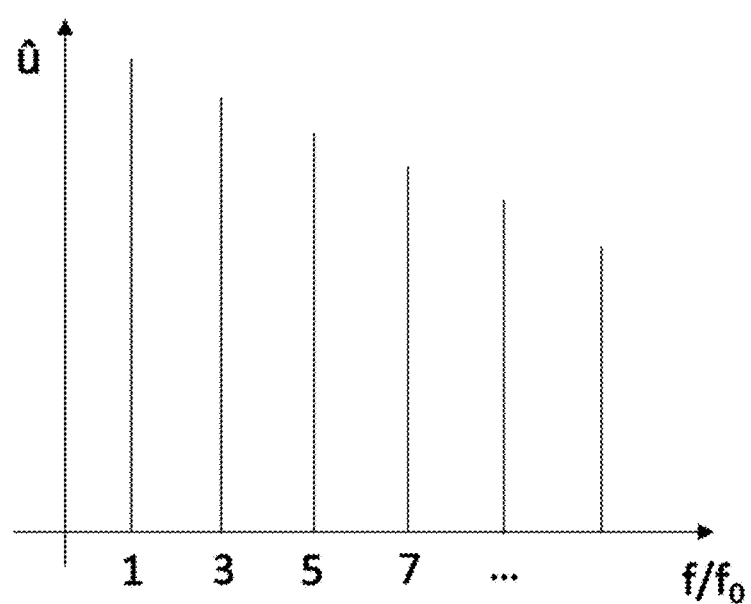

SYSTEMS AND METHODS FOR DETECTING MAGNETIC MARKERS FOR SURGICAL GUIDANCE

CROSS REFERENCE TO RELATED APPLICATIONS

This is the national phase under 35 U.S.C. § 371 of International Application No. PCT/GB2021/052290 filed on Sep. 6, 2021, which claims priority to and the benefit of United Kingdom Application No. 2013909.3 filed on Sep. 4, 2020, the entire disclosures of each of which are incorporated by reference herein.

FIELD OF THE DISCLOSURE

This disclosure relates in general to the field of surgical guidance; more specifically to systems and methods for detecting markers and tracers that aid in locating a site in the body; for example, a lesion for surgical excision.

BACKGROUND

Markers are used to guide surgeons to a region of interest during a surgical procedure, where the site of interest is not physically visible or palpable; for example, a small tumour that needs to be excised. The marker may be placed during a biopsy or other surgical procedure at a site of interest in the body; for example, a cancer lesion. Ideally, such a marker will be deployable through a narrow gauge needle. The marker is placed under imaging guidance such as ultrasound or X-ray/mammography. During subsequent surgery, the marker is detected and localised using a handheld probe which provides audible, visual or other feedback to the surgeon to guide the surgery. Typically the marker is excised along with the surrounding tissue.

A marker can also be used to mark a lymph node before a course of neo-adjuvant therapy. In this way a node can be readily identified after the neo-adjuvant therapy for excision, even if fibrosis from the therapy has affected the lymphatics so that conventional lymphatic tracers are not able to flow to the draining lymph nodes.

One such tumour-marking approach is to use a marker containing a radioisotope such as Iodine 90 which can be detected using a handheld gamma detection probe; e.g., a Geiger counter. However, the use of radioactive materials is closely regulated, making it challenging to set up a radioactive seed programme in all but the largest academic hospital centres.

A different approach is discussed in WO 2011/067576, WO 2014/013235 and WO 2014/140567, the contents of which are incorporated herein by reference, which uses magnetic fields and a magnetic marker with high magnetic susceptibility. A handheld probe generates an alternating field which excites a magnetically responsive marker, and detects the responding magnetic field.

Markers that are liquid or liquid-borne may also be used in a surgical procedure; for example in the detection of sentinel lymph nodes for a biopsy. Such markers may be referred to as "tracers". Sentinel lymph node biopsy is an important technique used to stage some cancers; that is to evaluate the spread of certain cancer types; particularly breast cancer. A tracer can be injected near a cancer tumour. The tracer particles are then taken up in the lymphatic system and flow to the draining lymph nodes where they accumulate. The nodes may then be located either by visual discoloration of the node or using a handheld probe so that they can be excised for pathological assessment. The nodes identified in this way are called 'sentinel' nodes because they are the ones to which the cancer may spread. The surgical procedure to identify and remove them is known as a sentinel lymph node biopsy procedure.

Typically, the two procedures—excision of the tumour and excision of the lymph nodes—happen in the same operation. Thus the tracer and marker can both be present in the breast or other tissue at the same time.

As above, one approach is to use a liquid marker containing a radioisotope; e.g., a technetium-99 m sulfur colloid. The radio-labelled colloid particles accumulate in the draining lymph nodes, which can then be identified for excision using a handheld gamma probe (Geiger counter). However, technetium-99 m has only a 6-hour half-life and so must be injected close to the time of surgery, thus creating a scheduling challenge. It may also have a complicated supply chain, and may not be available to isolated hospitals. There may also be interruptions in supply if a reactor producing the isotope is out of operation at a given time.

A different approach is to use a suspension of superparamagnetic iron oxide nanoparticles. These particles have no half-life, which means that they can be available in any hospital and can be injected a number of days before surgery, making scheduling more convenient.

The nanoparticles can be detected by a magnetic probe, such for example as the handheld probe mentioned above. However, such a probe may then respond to both a magnetic marker and an iron oxide nanoparticle suspension. In particular, a portion of the nanoparticle suspension may remain in the region of an injection site near the lesion. It is desirable to carry out a lesion removal procedure and a sentinel lymph node biopsy in a single surgery, but it has proved problematic to provide a detection system that is able to distinguish the lesion marker from other magnetically responsive materials. This is illustrated in FIG. 1A of the accompanying drawings.

Other magnetically responsive materials include surgical tools made from metal. It is desirable to develop magnetic markers or tracers that can be detected even in the presence of metallic tools. This is illustrated in FIG. 1B.

The human body itself has a magnetic response that can interfere with the detection of a magnetic marker because the water that is the main constituent of human tissue can give a diamagnetic response. Typically, a large amount of human tissue surrounds an injected marker during a localization procedure. A marker that can be accurately localized against a background signal from the human body would therefore be advantageous. This is illustrated in FIG. 1C.

Multiple markers may be present at the lesion site. For example, a biopsy marker may have previously been placed to monitor the evolution of the tumoral mass over time by means of mammography or ultrasound scans. It is desirable that a probe adapted for lesion localization during surgery should be only sensitive to the marker placed for this purpose. This is illustrated in FIG. 1D.

If a magnetic marker is used to mark a particular lymph node and a magnetic tracer is also used to map and identify other sentinel lymph nodes, then there may be one or more lymph nodes in which there is a magnetic marker and a magnetic tracer. It would be advantageous to be able to localize and identify which lymph nodes are marked and which only contain the tracer. It may also be advantageous to be able to quantify the amount of tracer in the node even in the presence of a marker. Thus, there is a need to discriminate between a marker and a tracer within a lymph node. This is illustrated in FIG. 1E.

One proposed solution to the above issues is to use a marker that responds non-linearly to an exciting magnetic field. It is possible to analyse the full harmonic response to discriminate the marker from tracers, metallic tools, the body or other markers that have a different and typically more linear response at the same field intensities.

Materials with a large Barkhausen discontinuity in the magnetisation curve, i.e. 'Large Barkhausen Jump' (LBJ) materials, undergo a rapid reversal of their magnetic polarization when excited by an external magnetic field whose field strength opposing the instantaneous magnetic polarization of the wire exceeds a predetermined threshold value, also known as a switching field. Thus, the marker exhibits bistable behaviour, reversing between two magnetic polarisation states. Each reversal of magnetisation generates a magnetic pulse with harmonic components. The profile and number of harmonics can be measured (out to many tens of harmonics) to identify the marker from other materials.

For detection purposes, it is desirable to use a high external magnetic field, which is able to excite the magnetic marker and, in particular, instigate the above-described bistable behaviour, at a sufficiently long range. However, secondary magnetic sources which may be background magnetic sources may also exhibit non-linearity at high magnetic fields. For instance, iron oxide nanoparticles used as a magnetic tracer may be generally linear but some non-linearity can be exhibited at high magnetic fields. This may be particularly problematic when a secondary magnetic source is distributed over a large region. Parts of the secondary magnetic source may be much closer to the probe than a magnetic marker and so may experience a correspondingly high magnetic field, and so may be especially likely to exhibit a problematic high-field non-linearity. As a user does not know the distribution or magnetic properties of a secondary magnetic source, it is difficult to compensate for these secondary signals and identify the desired marker.

In general, existing solutions have focused on making use of a small driving magnetic field only. It has been shown (see, for example, CA 3031282 A1) that some LBJ materials can exhibit a strong non-linear response even when the marker is shorter than a critical length and/or is excited below the switching field. Markers formed from such materials are known as sub-bistable markers. Other markers with a smaller level or different type of non-linearity in their magnetic response could also be considered for discrimination against more linear secondary signals. For example, non-linearity could be the result of inclusion of a non-linear electronic component in a marker; e.g. a diode.

Ideally, an exciting magnetic field generated by a magnetic probe (the drive field) should only include one frequency component at a fundamental frequency. Strong magnetic fields are also desirable to achieve suitably large detection distances. However, it is challenging to produce an alternating magnetic field around a probe with both a high field strength and a pure single-frequency sinusoidal waveform at a desired frequency. When an amplifier is driven with sufficient power to produce a strong field, some distortion or impurity is typically introduced in the sinusoidal waveform, which results in harmonics of the drive frequency being added.

Low distortion operational amplifiers can provide a harmonic distortion of about −120 dB, where harmonic distortion is the ratio of the rms (root mean square) value of a harmonic of interest ($2^{nd}$, $3^{rd}$, etc) to the rms signal level. However, such low distortion may be achieved only at currents of tenths of a milliamp, which are generally too low. In general, such amplifiers also use resistive loads, while magnetic probes typically use inductive loads. Further, the harmonic distortion of operational amplifiers is typically measured by looking at voltages rather than current. However, in the case of detecting magnetic markers of the kind described herein, relevant harmonic distortion occurs in the exciting magnetic field, which is generated from a current rather than a voltage. It is therefore not straightforward to produce highly pure drive fields with off-the-shelf electronic components.

A typical optimized harmonic distortion for a drive field in a magnetic probe, such as that in WO 2011/067576, WO 2014/013235 or WO 2014/140567, may be in the range of −70 dB to −100 dB at the frequencies of interest. This indicates harmonic components less than 10,000 to 100,000 times smaller than the drive signal, which is acceptable for most applications that rely on linear detection and even for high-end audio systems. However, for detecting magnetic markers of the kind described, such a level of harmonic distortion in the drive, when reflected by a linear magnetic material near to the probe, may easily be as large as the signal from a non-linear marker at some distance from a probe.

Thus, there is a need to provide a system for detecting a magnetic marker or tracer in a human or animal body for use in surgical guidance that is able to distinguish a non-linear marker from other magnetically responsive materials even with a non-pure drive field. The present disclosure aims to address this need.

U.S. Pat. No. 5,793,289 discloses a harmonic electronic article surveillance (EAS) system of the kind that is used in a different field from the present disclosure; namely to detect the presence of a marker in an interrogation zone, to prevent or deter theft of merchandise from retail establishments. A marker which includes a magnetic element produces a detectable marker signal in the form of perturbations of an alternating interrogation signal field radiating within the interrogation zone. The marker signal includes harmonic signal components at harmonics of the operating frequency of the interrogation signal. The interrogation signal has the form of discrete pulses, which allows the effective frequency of the interrogation signal to be increased without exceeding regulatory limits on the average radiated power. Detecting circuitry may be arranged so that it does not operate to detect the marker signal at times that do not correspond to the discrete pulses, thereby reducing the possibility of false alarms in response to impulsive noise. The timing of the pulses may be adjusted so that the pulses do not coincide with a periodically recurring noise signal. Further, the amplitude of the interrogation signal pulses may be reduced when a signal is detected that is similar in shape to a marker signal but has an amplitude in excess of a predetermined threshold level, making it possible to distinguish between signals that are generated by a marker and signals generated by objects such as shopping carts that may tend to generate signals that mimic marker signals in response to high-level interrogation signals.

However, the EAS system of U.S. Pat. No. 5,793,289, which is adapted to detect the presence of a marker in a relatively huge interrogation zone in a retail store, for example, is unuitable for detecting a magnetic marker or tracer in a body for surgical guidance. The generation of a pulsed interrogation signal, with substantially no amplitude between discrete pulses, would give rise to unwanted thermal effects within the signal generator, leading to inaccuracies, while the detection of a marker within a body relies on the accurate detection of subtle changes of magnetic field.

SUMMARY OF THE DISCLOSURE

According to one aspect of the present disclosure, there is provided a method for detecting a magnetic marker for guiding a surgeon to a region of interest during a surgical procedure, the method comprising generating a driving magnetic field having a repeating pattern of two or more successive periods of time, the driving magnetic field having a substantially constant, non-zero amplitude during each of the successive periods of time, and the amplitude of the driving magnetic field during at least one of the periods of time being different from the amplitude of the driving magnetic field during at least one other of the periods of time; detecting a response magnetic field; selecting at least one signal from a plurality of sensed signals, each of which corresponds to the response magnetic field detected during a respective one of the successive periods of time of each cycle; determining a detection signal corresponding to the magnetic marker using the at least one selected signal; and generating an output signal based on a strength of the detection signal.

In another aspect, the present disclosure comprehends a magnetic detection system for detecting a magnetic marker for guiding a surgeon to a region of interest during a surgical procedure, the magnetic detection system comprising a driving unit configured to generate a driving magnetic field having a repeating pattern of two or more successive periods of time in which the driving magnetic field has a substantially constant, non-zero amplitude during each of the successive periods of time, and the amplitude of the driving magnetic field during at least one of the periods of time is different from the amplitude of the driving magnetic field during at least one other of the periods of time; a magnetic field sensor configured to detect a response magnetic field; a processor configured to select, based on the response magnetic field, at least one signal from a plurality of sensed signals, each of which corresponds to the response magnetic field detected during a respective one of the successive periods of time of each cycle; determine a detection signal corresponding to the magnetic marker using the at least one selected signal; and generate an output signal based on a strength of the detection signal.

In some embodiments, the output signal may be used to control operation of a user interface device such, for example, as a sound generator (e.g. a speaker), a haptic device and/or a display, for outputting the output signal in a form that is perceptible by a user. Thus, in some embodiments, the output signal may comprise an audio signal, a haptic signal and/or a display signal. In some embodiments, the output signal may comprise a user-feedback signal that is based on a marker proximity value, as disclosed for example by copending International application no. PCT/GB2021/051750, the contents of which are incorporated herein by reference. The marker proximity value may thus be determined on the basis of the detection signal. In this sense, it will be understood that the output signal represents an output of the methods or systems of the invention which conveys information relating to detection of the magnetic marker; it does not mean the driving magnetic field which is output by the driving unit.

It will be understood that references herein to a substantially constant, non-zero amplitude or to a "different" amplitude of the driving magnetic field are to the amplitude of the driving magnetic field at a substantially constant distance from a source of the driving magnetic field. Equally, a driving magnetic field of substantially constant amplitude may be thought of as a driving magnetic field which is generated using a driving signal as disclosed herein of substantially constant amplitude.

Typically, the amplitude of the driving magnetic field during at least one of the successive periods of time is high in relation to the the amplitude of the driving magnetic field during at least one other of the successive periods of time, being calculated to give rise to a non-linear response in the magnetic marker. The amplitude of the driving magnetic field during at least one other of the successive periods of time may be relatively low in comparison to the the amplitude of the driving magnetic field during at least one of the successive periods of time, being calculated to give rise to a substantially linear response in a tracer or any other magnetic material formed of non-LBJ material which may be present in the vicinity of the marker. It will be appreciated that the driving unit may be configured such that the strength of the driving magnetic field is tailored for use with one or more specific magnetic markers or tracers. A typical magnetic marker may comprise less than about 5 mg of a LBJ material. Thus, in some embodiments, the driving unit may comprise a probe which is configured to produce a driving magnetic field having a maximum field strength in at least one of the successive periods of time of between about 100 µT and about 2000 µT within about 5 mm of the probe.

The driving magnetic field in at least one of the successive periods of time may have an amplitude which is less than the maximum field strength. For example, in some embodiments, the driving magnetic field in at least one of the successive periods of time may have an amplitude which is between about 10-90% of a maximum amplitude which corresponds to the maximum field strength of the driving magnetic field. In some embodiments, the driving magnetic field in at least one of the successive periods of time may have an amplitude which is between about 25-75% of the maximum amplitude of the driving magnetic field. Typically, the driving magnetic field may have an amplitude in at least one of the successive periods of time which is between about 25-50%, e.g. about 33%, of the maximum amplitude of the driving magnetic field. Where the cyclic pattern of the driving magnetic field comprises more than two successive periods of time, the driving magnetic field may have different field strengths in two or more respective periods of time which are a fraction of the maximum field strength, within the ranges described above.

The methods of the present disclosure thus comprehend detecting the response magnetic field during each of the successive periods of time of the cyclic pattern to generate the plurality of sensed signals which correspond to the respective successive periods of time. At least one of the sensed signals is then selected for the detection signal corresponding to the magnetic marker, and the output signal is based on the strength of the detection signal. The methods of the present disclosure may therefore involve analysing the plurality of sensed signals from the successive periods of time of the cyclic pattern as disclosed herein to determine a suitable detection signal.

Preferably, the two or more successive periods of time forming the cyclic pattern may be contiguous, such that the successive periods of time are uninterrupted and the amplitude of the driving magnetic field is never zero during performance of the methods of the disclosure. However, in some embodiments, one or more short gaps of no or nearly no field between successive periods of time of positive driving field may be permitted. Thus, in some embodiments, two or more of the successive periods of time forming the cyclic pattern may be non-contiguous, with one or more short intervals between successive periods of time in which the amplitude of the driving magnetic field is zero or nearly zero. However, for reasons discussed herein, such intervals should be minimized and may, for example, cumulatively comprise less than about 25%, preferably less than 10%, more preferably less than 5%, and most preferably less than about 1% of the total duration of the cyclic pattern.

In accordance with the methods and systems of the present disclosure, the response magnetic field is detected continuously across the substantially the whole of the repeating pattern of successive time periods during which the amplitude of the driving magnetic field is varied from one period of time to another in accordance with the pattern, and each successive period of time gives rise to a different respective sensed signal which depends on the amplitude of the driving magnetic field during that period of time as well as the presence of a marker, tracer and/or other secondary sources of magnetic material. The methods and systems of the present disclosure comprehend selecting one or more of the sensed signals and determining a detection signal which corresponds to the marker using the one or more selected signals. Thereafter, the output signal is generated, based on a strength of the detection signal.

The duration of the successive periods of time within each cycle may be the substantially same or different from one another. The driving magnetic field may conveniently comprise a substantially constant frequency during all of the successive periods of time.

In some embodiments, the cyclic pattern may comprise two successive periods of time. The response magnetic field which is detected during each of the successive periods of time may comprise a first response component at a first frequency and a second response component at a second frequency which is different from the first frequency.

In accordance with another aspect of the present disclosure therefore, there is provided a method for detecting a magnetic marker for guiding a surgeon to a region of interest during a surgical procedure, the method comprising generating a driving magnetic field comprising a first frequency, the driving magnetic field having a first amplitude for a first period of time and a second amplitude, lower than the first amplitude, for a second period of time; detecting a response magnetic field comprising a first response component at the first frequency and a second response component at a second frequency which is different from the first frequency; selecting at least one signal from a first sensed signal corresponding to the response magnetic field detected during the first time period and a second sensed signal corresponding to the response magnetic field detected during the second time period; determining a detection signal corresponding to the magnetic marker using the at least one selected signal; and generating an output signal based on a strength of the detection signal.

Suitably, the selecting, determining and generating steps may be perfomed by a processor.

It will be understood in accordance with the present disclosure, that the first and second time periods are different from one another, in the sense that they are not simultaneous. Suitably, the first and second time periods are mutually consecutive; preferably without any interruption between them. In this way, the amplitude of the driving magnetic field is never zero during operation of the method. The first and second amplitudes are advantageously both non-zero, which helps to minimize unwanted thermal effects and potential inaccuracies, as described herein.

Thus, the step of generating the driving magnetic field may comprise alternating between the first amplitude and the second amplitude.

In some embodiments, the step of selecting the at least one signal may be based on identifying the presence of a secondary magnetic source, such for example as a liquid magnetic tracer.

The step of identifying the presence of the secondary magnetic source may comprise calculating a harmonic ratio between the first response component at the first frequency and the second response component at the second frequency. Suitably, a first harmonic ratio based on one of the plurality of sensed signals, for example the first sensed signal, may be compared with a second harmonic ratio based on another of the sensed signals, for example the second sensed signal.

In some embodiments, the step of identifying the presence of a secondary magnetic source may be based on comparing a spectral analysis of the response magnetic field with pre-recorded responses from an isolated magnetic marker and an isolated secondary source.

In some embodiments, the step of selecting the at least one signal may be based on an absolute magnitude of at least one of the plurality of sensed signals, e.g. the first sensed signal and/or the second sensed signal; for example, whether the absolute magnitude of one or more of the sensed signal exceeds a predetermined threshold.

In yet another aspect, the present disclosure comprehends a magnetic detection system for detecting a magnetic marker for guiding a surgeon to a region of interest during a surgical procedure, the magnetic detection system comprising a driving unit configured to generate a driving magnetic field comprising a first frequency, the driving magnetic field having a first amplitude for a first period of time and a second amplitude, lower than the first amplitude, for a second period of time; a magnetic field sensor configured to detect a response magnetic field comprising a first response component at the first frequency and a second response component at a second frequency different from the first frequency; a processor configured to select, based on the response magnetic field, at least one signal from a first sensed signal corresponding to the response magnetic field detected during the first time period and a second sensed signal corresponding to the response magnetic field detected during the second time period; determine a detection signal corresponding to the magnetic marker using the at least one selected signal; and generate an output signal based on a strength of the detection signal.

Other features of the present disclosure are described below and/or set out in the claims.

BRIEF DESCRIPTION OF THE DRAWINGS

For a better understanding of the present disclosure and to show more clearly how it may be carried into effect, reference will now be made by way of example only, to the accompanying drawings, in which:

FIG. 5A is a chart showing a magnetisation curve for an exemplary marker;

FIG. 5B is a chart showing a magnetic response in a time domain;

FIG. 5C is a chart showing a magnetic response in a frequency domain;

DETAILED DESCRIPTION

The present disclosure relates to a detection system and method for characterizing a marker, more particularly a magnetic marker, that can be implanted for marking a target site in the body, and to the detection and localisation of the implanted marker using a handheld probe.

The marker may be implanted in a site requiring marking in the body. This may, for example, be a tumour or other lesion or site of interest in soft tissue. Examples include, but are not limited to, benign lesions, cancerous lesions and lymph nodes. The marker may be placed in or near a lesion, or multiple markers may be placed to mark the margins or perimeter of a surgical site; for example the margins of a tumour or soft tissue sarcoma.

Figure 1A:
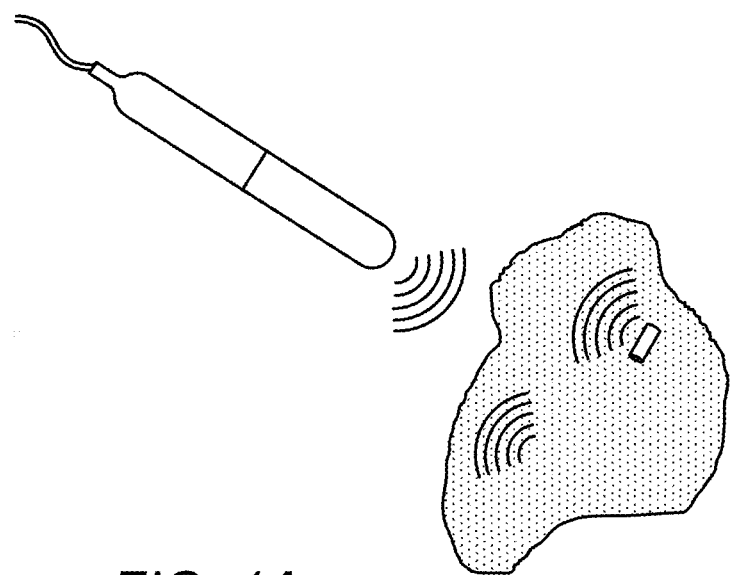
FIGS. 1A to 1E are illustrations indicating usage scenarios for an embodiment.
Figure 1B:
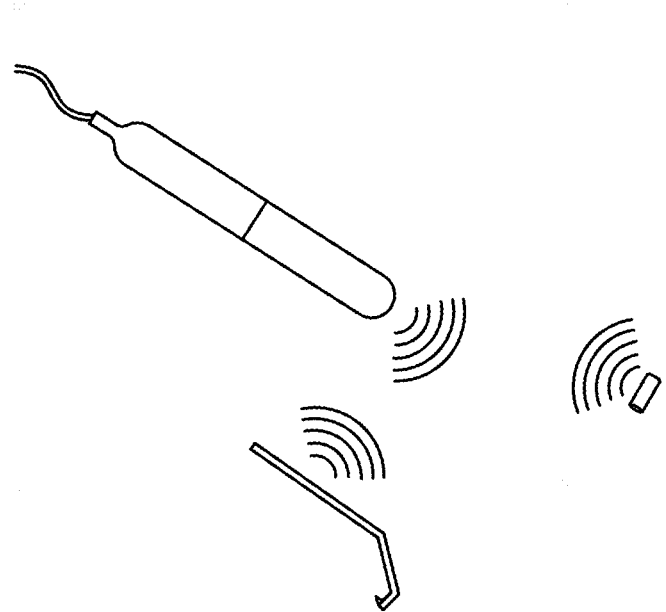
Figure 1C:
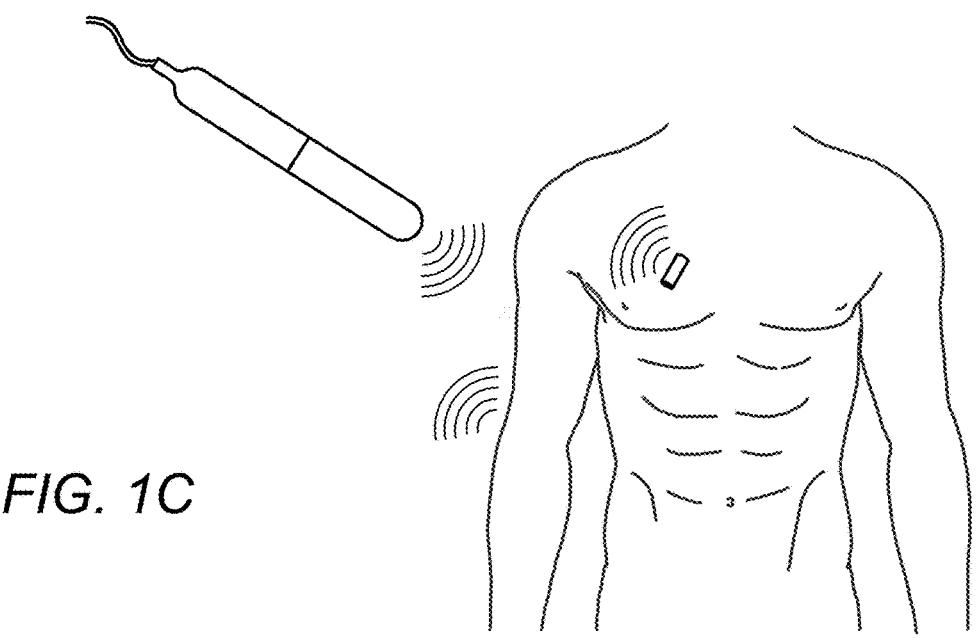
Figure 1D:
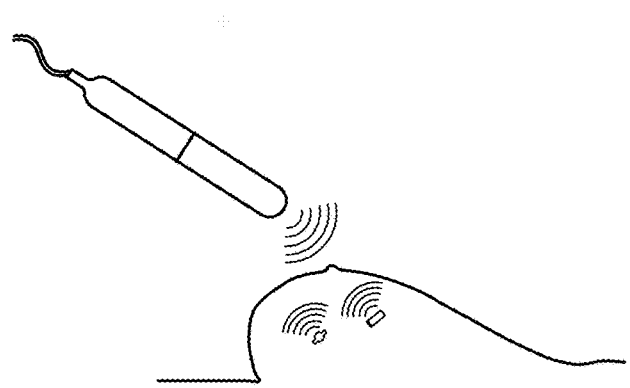
Figure 1E:
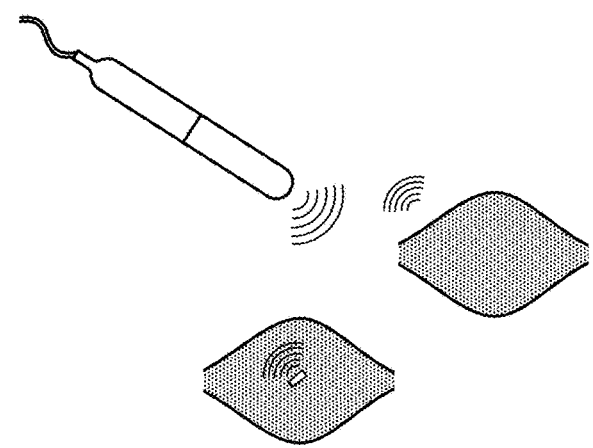
Figure 2:
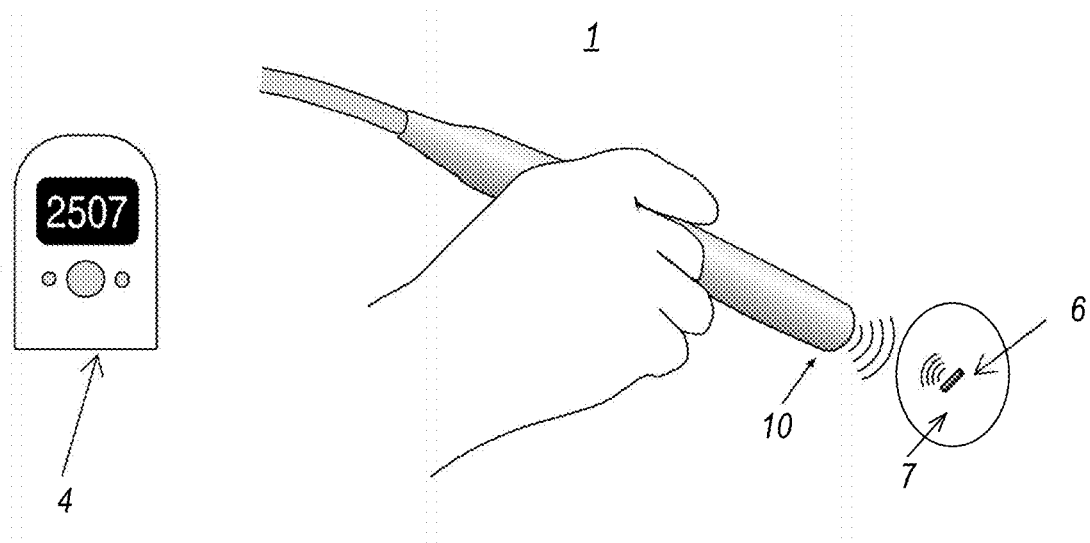
FIG. 2 is a schematic diagram of a magnetic detection system according to an embodiment of the present disclosure.

FIG. 2 of the accompanying drawings shows a schematic diagram of an embodiment of a detection system and marker according to the present disclosure. The detection system 1 comprises a probe 10 connected to a base unit 4. The probe 10 has one or more drive coils that generate an alternating magnetic field to excite a magnetic marker 6. A magnetic tracer 7 may also be present near or in the vicinity of the marker 6.

The marker 6 comprises at least one piece of magnetically responsive material and may have anon-linear magnetic susceptibility. A magnetisation of the material may respond in a non-linear fashion to an external magnetic field. The material may have a large Barkhausen discontinuity in its magnetisation curve, and may be known as a "large Barkhausen jump material", an "LBJ material", a "bistable switching material" or a "material with large non-linearities in its magnetisation curve". For example, when a length of LBJ material is exposed to an external magnetic field whose field strength opposing the instantaneous magnetic polarization of said length of material exceeds a predetermined threshold value, the switching field HSW, its magnetic polarization undergoes a rapid reversal. This reversal of magnetisation generates a magnetic pulse with intense harmonic components.

The tracer 7 typically comprises a liquid comprising a plurality of magnetic nanoparticles. For example, the tracer 7 may comprise a plurality of iron oxide nanoparticles. The tracer 7 is an example of a secondary magnetic source. In some cases, the tracer 7 may be considered to be a background magnetic source. The nanoparticles may be described as superparamagnetic nanoparticles. When the tracer 7 is exposed to an external field the magnetic response may be substantially linear; that is, the magnetisation of the tracer 7 is directly proportional to the applied field. The magnetic response of the tracer 7 may be substantially linear when a strength of the external field is within a certain range. When the strength of the external magnetic field is greater than a certain linear threshold, the magnetisation of the tracer 7 may saturate, leading to a non-linear magnetic response.

The probe 10 of the detection system further contains one or more sense coils arranged to detect the changes in the magnetic field caused by the change in magnetisation of the marker 6 and/or tracer 7.

To detect a marker 6 in a typical lesion or site of interest, the probe 10 should ideally have a detection depth of at least 30 mm, preferably more than 40 mm, and more preferably greater than 50 mm. Ideally, the marker 6 gives the same magnitude of response regardless of the direction in which the marker 6 is approached, i.e. it should have a low anisotropy of magnestisation. This is to provide consistent feedback to a surgeon as to the location of the marker 6 relative to the probe 10.

Figure 3:
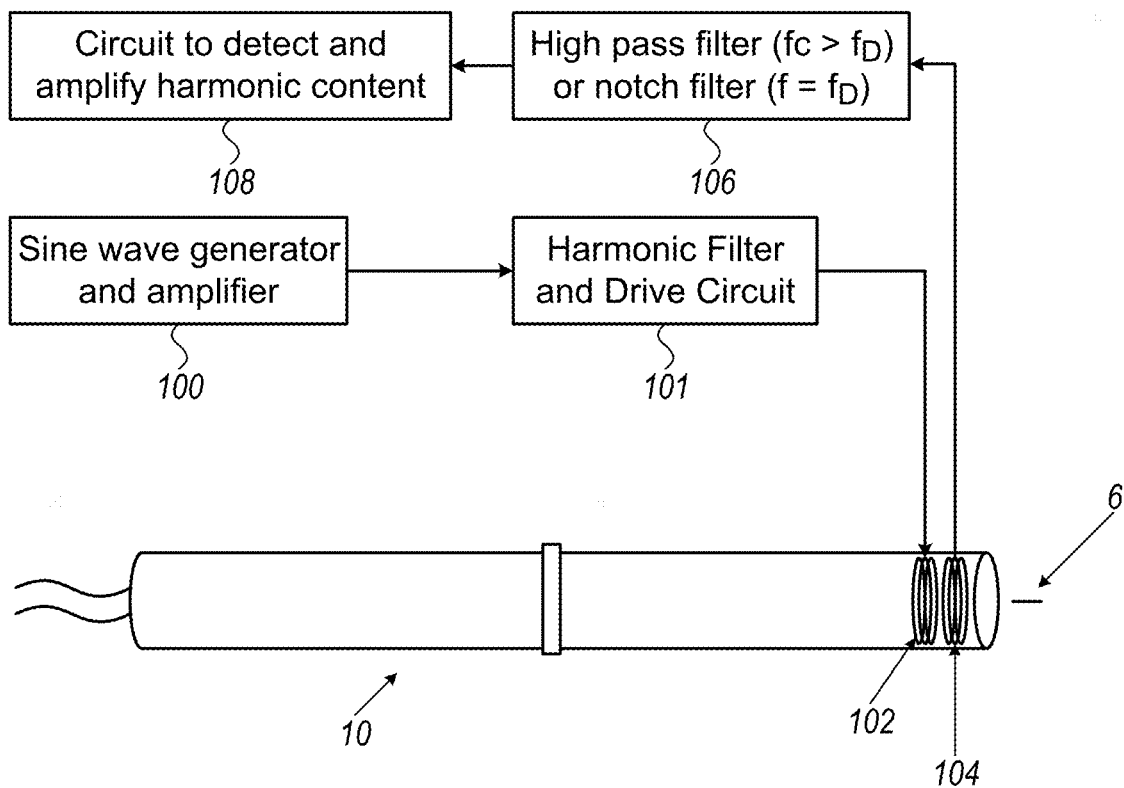
FIG. 3 is a schematic diagram of a magnetic detection system according to an embodiment of the present disclosure.

FIG. 3 illustrates an example probe 10 in more detail. The detection probe 10 comprises a drive coil 102 to generate a driving magnetic field and a sense coil 104 to detect a response magnetic field.

The drive coil 102 is configured to generate the driving magnetic field by means of an applied electrical current, comprising a driving signal. The driving magnetic field is an alternating magnetic field generated to alternate at a fundamental frequency component $f_1$. The drive coil 102 may suitably be configured to generate the driving magnetic field at one or more different output amplitudes.

The base unit 4 and probe 10 may further comprise a sine wave generator and amplifier 100 and a harmonic filter and drive circuit 101, configured to generate the driving signal at the fundamental frequency $f_1$. The sine wave generator and amplifier 100 is configured to generate and amplify an alternating current driving signal configured to alternate at the fundamental frequency $f_1$. The amplifier 100 is configured to amplify the driving signal to one or more different amplitude levels. The amplifier 100 may be configured to amplify the driving signal to one of at least two distinct amplitude levels at a given time. For example, two distinct amplitude levels may be referred to as $A_{LOW}$ and $A_{HIGH}$, wherein $A_{HIGH}$ is greater than $A_{LOW}$. Advantageously, as described herein, the driving signal may oscillate between $A_{LOW}$ and $A_{HIGH}$ without interruption. Thus, $A_{HIGH}$ and $A_{LOW}$ may both be non-zero. $A_{HIGH}$ may suitably be of substantially constant amplitude. $A_{LOW}$ may be of substantially constant amplitude. In some embodiments, the driving signal may have a continuous fundamental frequency $f_1$.

Figure 4:
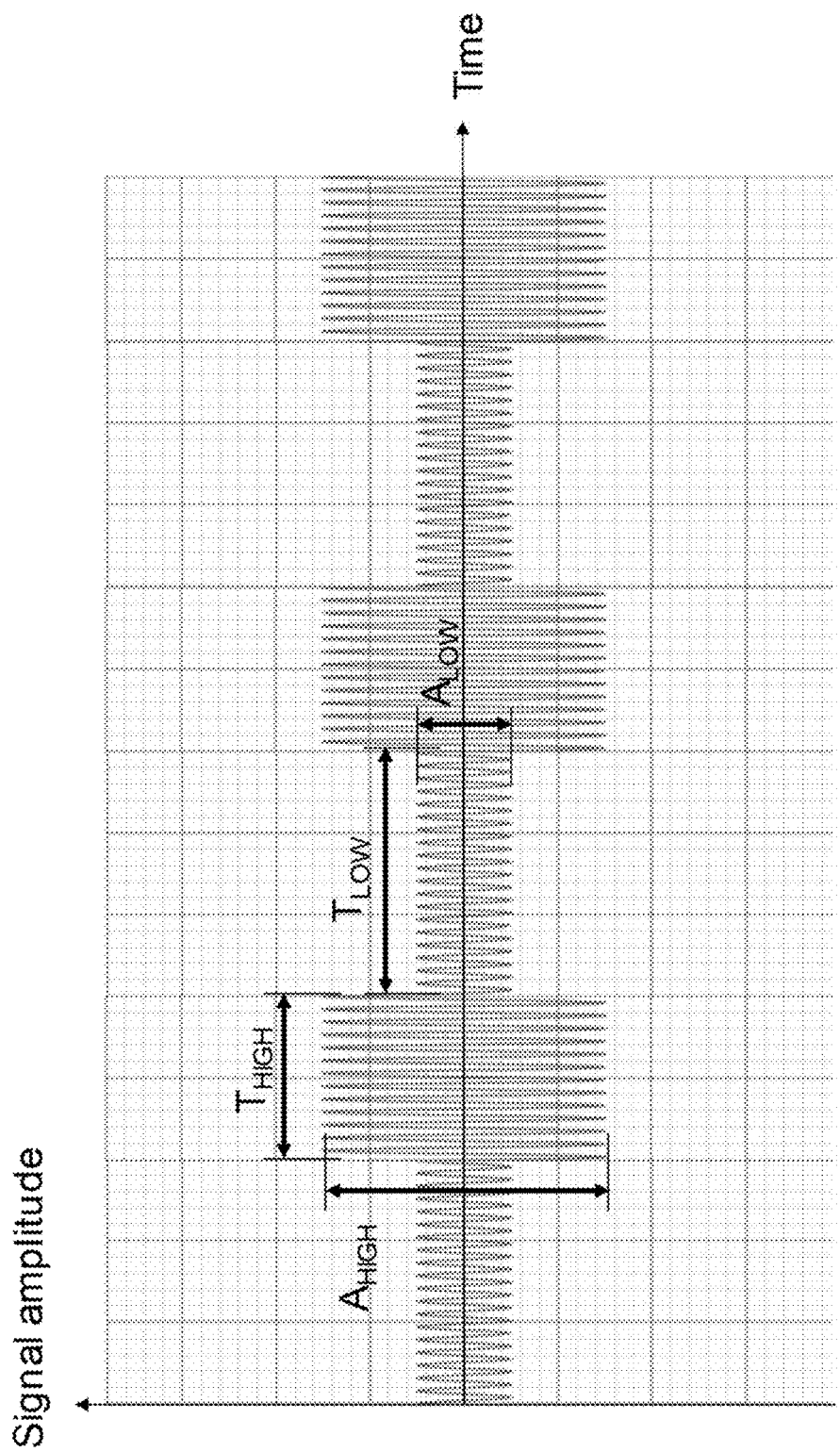
FIG. 4 shows an exemplary driving signal in accordance with the present disclosure.

By way of illustration, an example of a suitable, uninterrupted driving signal is illustrated in FIG. 4. The driving signal of FIG. 4 consists of a cyclic pattern of two successive periods of time during each of which the driving signal has a substantially constant, non-zero amplitude. The amplitude $A_{LOW}$ of the driving signal during one of the periods is different from the amplitude $A_{HIGH}$ of the driving signal during the other of the period of time. It will be appreciated however, that in accordance with the present disclosure, the driving signal may consist of a cyclic pattern of more than two successive periods of time, the driving signal having a substantially constant, non-zero amplitude during each of the successive periods of time, and the amplitude of the driving signal during at least one of the periods of time being different from the amplitude of the driving signal during at least one other of the periods of time. For example, the driving signal may have a cyclic pattern of three successive periods of time. During each of the three successive periods of time, the driving signal may have a substantially constant, non-zero amplitude. The amplitude of the driving signal during one of the periods of time may be different from the amplitude of the driving signal during the other two periods of time, or the amplitude of the driving signal may be different during all three periods of time.

The resulting driving magnetic field may therefore have at least two distinct field strength values $H_{LOW}$ and $H_{HIGH}$. The driving magnetic field may alternate between $H_{LOW}$ and $H_{HIGH}$. The driving magnetic field may alternate according to a predetermined duty cycle. The drive coil 102 may output the driving magnetic field at the amplitude $H_{HIGH}$ for a first period of time $T_{HIGH}$. The drive coil 102 may output the driving magnetic field at the amplitude $H_{LOW}$ for a second period of time $T_{LOW}$. The duty cycle ratio may be 50% or, in some implementations it may be between about 25% and about 75%. The total duty cycle time period $T_{HIGH}+T_{LOW}$ may be between about 10 ms and about 1000 ms. In some implementations $T_{HIGH}+T_{LOW}$ may be about 100 ms. In the example driving signal of FIG. 4, $T_{HIGH}$ is shorter in duration than $T_{LOW}$. Suitably, in some embodiments, the driving magnetic field may have a maximum field strength, e.g. $H_{HIGH}$, of between about 100 μT and about 2000 μT within about 5 mm of the probe 10.

The harmonic filter and drive circuit 101 is configured to filter the driving signal and provide the driving signal to the drive coil 102. The harmonic filter is configured to reduce one or more additional frequency components $f_n$ in the driving signal. Suitably, the harmonic filter may be a notch filter tuned to a specific harmonic. The filtered driving signal is provided to the drive coil 102 to generate the driving field.

The base unit may further comprise one or more processing units; for example, a microcontroller and/or a Field Programmable Gate Array (FPGA). The base unit may further comprise a memory unit, an analogue to digital converter (ADC) and a digital to analogue converter (DAC). The memory unit may, for example, be formed of SD RAM, or any suitable volatile or nonvolatile storage. The microcontroller may further control and interact with a computer memory. The microcontroller may, for example, be a STM32F769 microcontroller from STM Electronics, or any other suitable microcontroller. The microcontroller and FPGA may generate the sine wave drive signal which is then converted to an analogue signal by the DAC before being amplified; for example using an operational amplifier.

The sense coil 104 is configured to generate an electrical sensed signal in response to a varying external magnetic field. The sense coil 104 is arranged to detect a response magnetic field generated by a magnetic material in response to the driving magnetic field. For example, the sense coil 104 may be arranged to detect a response magnetic field generated by a marker 6 and/or a tracer 7.

The detection probe 10 further comprises an electronic filter 106, e.g. a notch filter, and a circuit to detect and amplify harmonic content 108. The electronic filter 106 may suitably be configured to reduce or remove the fundamental frequency $f_1$ from the sensed signal, to improve the sensing of other frequency components $f_n$ of the sensed signal. The circuit to detect and amplify harmonic content 108 may further amplify one or more of additional frequency components $f_n$ of the sensed signal, e.g., corresponding to one or more harmonic frequencies of the fundamental frequency $f_1$. The circuit may also suppress unwanted frequency components. The operation of the components for processing the sensed signal is described in more detail below.

FIG. 5A shows a possible magnetisation curve of the magnetic marker 6. The curve shows the level of magnetisation B of the marker 6 in relation to the strength of an applied external magnetic field H. The marker 6 may comprise at least one piece of a large Barkhausen jump material (LBJ). As described above, the LBJ material may have a non-linear magnetisation curve. According to the magnetisation curve, an excitation field H which is lower than the switching field 25 will result in little or no change to the magnetisation B, except for a small change in magnitude which is represented by the change from point 24 to point 25. In particular, an excitation field H which is lower than the switching field 25 will not effect a change in the polarity of magnetisation B of the marker 6. The magnetisation curve shows a reversal of magnetisation once the switching field, indicated at 25, is exceeded. The curve also shows a hysteresis effect, with a further reversal of magnetisation once the switching field indicated at 30 is exceeded. In this way, reversal of magnetization of the marker 6 occurs regularly in time with half the time period (double the frequency) of the driving frequency.

FIG. 5B shows a typical sensed signal corresponding to the magnetisation curve of FIG. 5A. When the marker 6 is excited by an alternating field with a sufficiently high amplitude, e.g. $A_{HIGH}$, pulses corresponding to the reversal of magnetisation are seen in the time domain. The pulses may be superimposed onto a sine wave, if a spurious driving magnetic field coupled into the sense coils is not filtered out fully. As discussed in more detail below, a material having a linear magnetic response would produce a sinusoidal sensed signal at the same frequency as the driving magnetic field. In comparison, the non-linear response of the marker 6 produces many harmonic frequency components in the sensed signal, which combine in superposition to produce the resulting pulse signal, e.g. shown in FIG. 5B.

FIG. 5C illustrates the sensed signal corresponding to the magnetisation curve of FIG. 5A in the frequency domain. In response to the driving magnetic field, e.g. $H_{HIGH}$, substantially at the fundamental frequency ($f_1$), the sensed signal comprises at least one additional frequency component at a higher harmonic frequency. As indicated, the sensed signal may comprise a significant component in each of at least the 2nd to 10th harmonic frequencies ($f_2$-$f_{10}$) with respect to the fundamental frequency. Higher frequency components may also be present.

The marker 6 may be configured to provide a significant response at a specific harmonic frequency ($f_X$) Such harmonic frequency $f_X$ may be utilised to distinguish between a portion of the sensed signal generated by the marker 6 and another portion of the sensed signal which may be generated by one or more other secondary magnetic sources. For example, the harmonic frequency $f_X$ may be utilised to distinguish between the marker 6 and the tracer 7. In some implementations, the third harmonic frequency ($f_3$) may be utilised to distinguish between the marker 6 and the tracer 7.

In the response magnetic field generated by the marker 6, a ratio between a fundamental frequency response and a particular harmonic frequency $f_X$ may be referred to as a marker response factor, or primary response factor. The marker response factor may be approximately 100 or may be less than 100. In some implementations, the marker response factor may be less than 50, for example, the marker response factor may be approximately 30 before any filter is applied.

Instead of operating in bistable mode, in some implementations the non-linear marker may function in a sub-bistable mode. As described above, some LBJ materials still exhibit a non-linear response at fields smaller than the switching field (e.g. the third harmonic H3 response) that is almost two orders of magnitude larger than for non-LBJ materials. This may allow detection of a marker which is further away from the probe 10, where driving fields are smaller, e.g. below the switching field for the marker. However, to generate an exciting field at longer distances from the probe 10, the field amplitude in proximity to the probe 10 will be much higher.

Figure 6A:
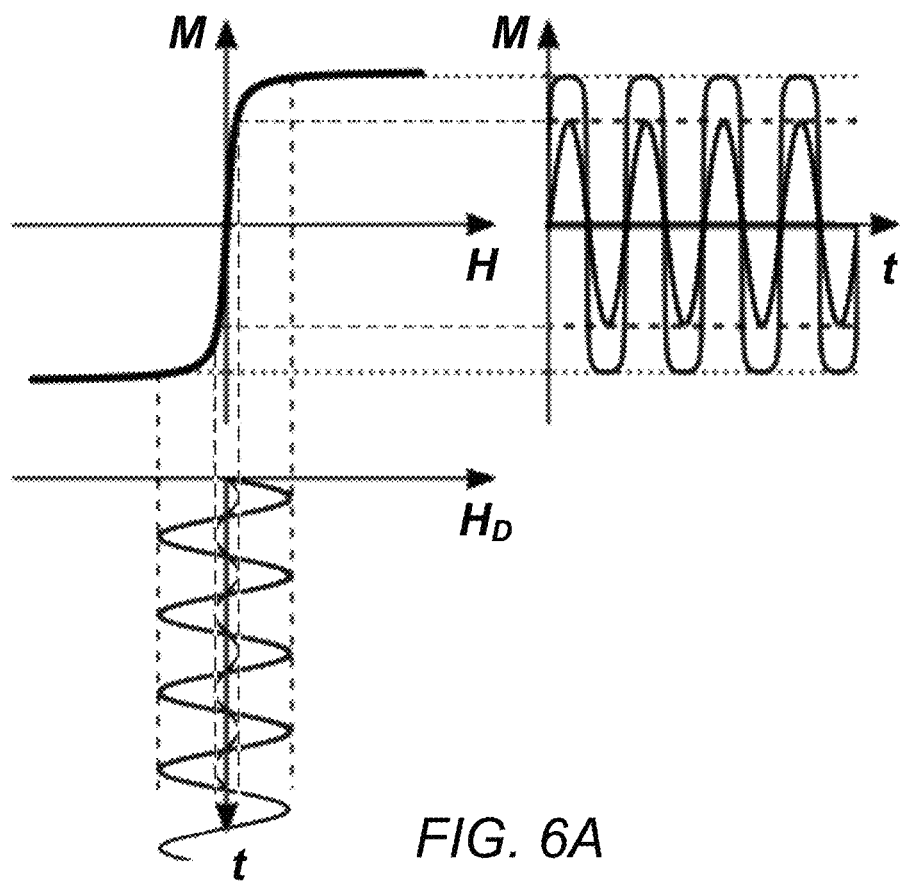
FIG. 6A is a chart showing a magnetisation curve for an exemplary tracer.

FIG. 6A shows a typical magnetisation curve for a magnetic tracer 7. The curve shows the level of magnetisation M of the tracer 7 in relation to the strength of an applied external magnetic field H. The magnetic response of the tracer 7 is substantially linear at low excitation fields. In higher external magnetic fields, the magnetisation of tracer 7 may saturate, as the nanoparticles in the tracer 7 fully align with the external magnetic field. The magnetic response of the tracer 7 is therefore linear in a low excitation field, and may become non-linear in response to a higher excitation field. According to the magnetisation curve, a sinusoidal excitation field H, having an amplitude lower than a certain linear threshold will result in a corresponding sinusoidal magnetisation M. An excitation field having an amplitude higher than the linear threshold may produce distortions in the corresponding magnetisation, i.e. a non-linearity. In addition, if a central part of the magnetisation curve is not linear (i.e. having a constant gradient), then further non-linear distortions in the corresponding magnetisation may be produced.

Figure 6B:
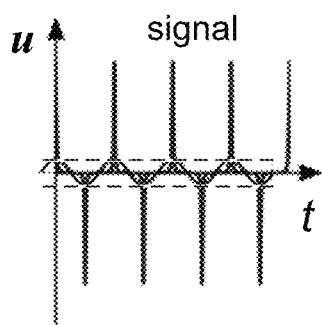
FIG. 6B is a chart showing a magnetic response in the time domain.

FIG. 6B shows a typical sensed signal corresponding to the magnetisation curve of FIG. 6A. When the tracer 7 is excited by an alternating field with an amplitude lower than the certain linear threshold mentioned in the previous paragraph, the sensed signal corresponds linearly to the excitation field. Where the alternating field has a sinusoidal form, the sensed signal therefore has a corresponding sinusoidal form. When the tracer 7 is excited by an alternating field with a sufficiently high amplitude, pulses corresponding to saturation of the tracer 7 magnetisation may be seen in the time domain. The non-linear response produces one or more harmonic frequency components in the sensed signal, which combine in superposition to produce the resulting pulse signal.

Figure 6C:
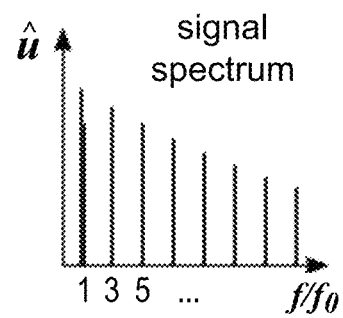
FIG. 6C is a chart showing a magnetic response in the frequency domain.

FIG. 6C illustrates the sensed signal corresponding to the magnetisation curve of FIG. 6A in the frequency domain. As can be seen, in response to the low-amplitude driving magnetic field substantially at the fundamental frequency ($f_1$), the sensed signal comprises primarily the fundamental frequency ($f_1$). In response to the high-amplitude driving magnetic field substantially at the fundamental frequency ($f_1$), the sensed signal comprises at least one additional frequency component at a higher harmonic frequency. As shown, the sensed signal may comprise a significant component in any of at least the 2nd to 10th harmonic frequencies ($f_2$-$f_{10}$) with respect to the fundamental frequency. In particular, there may be a significant component in the odd harmonic frequencies, and in the third harmonic in particular. Higher frequency components may also be present.

Harmonic frequency components in the sensed signal generated by the tracer 7 can interfere with the detection of harmonic frequency components generated by the marker 6, and may impede accurate detection of the marker 6.

As described above, the marker 6 may be configured to provide a significant response in a harmonic frequency $f_X$. The harmonic frequency $f_X$ may be utilised to distinguish between the portion of the sensed signal generated by the marker 6 and the portion generated by one or more other secondary magnetic sources. However, generation of a sensed signal component at the harmonic frequency $f_X$ by the tracer 7 may inhibit accurate detection of the marker 6. Generating a driving magnetic field with an amplitude below the linear threshold for the tracer 7 may reduce the generation of harmonic frequency components by the tracer 7. In particular, using a low amplitude driving magnetic field may reduce the generation of third harmonic frequency components by the tracer 7. However, using a low amplitude driving magnetic field may limit the detection range for detecting the marker 6.

In the response magnetic field generated by the tracer 7, a ratio between a fundamental frequency response and third harmonic frequency may be referred to as a secondary response factor. The driving coil 102 may be configured to generate alternately a low amplitude driving field $H_{LOW}$ and a high amplitude driving field $H_{HIGH}$ during the respective time periods $T_{LOW}$ and $T_{HIGH}$, as described above. Based on the signals sensed by the sense coil 104 during the time, and by comparing the response from $T_{LOW}$ with the response from $T_{HIGH}$, it can be determined whether a secondary source is present. For example, it can be established whether or not a tracer 7 is present in the vicinity of the probe 10. The magnetic detection system 1 is configured to determine, based on the comparison of response signals, whether it is appropriate to use the response from $T_{LOW}$ or the response from $T_{HIGH}$, in order to localise the marker 6.

In the event that a tracer 7 is determined to be present, it may be more appropriate to use the response signal from $T_{LOW}$, because the response of the tracer 7 to the driving field $H_{LOW}$ may be more linear, and will inhibit less accurate detection of the marker 6. In this way, a more accurate detection may be achieved in the presence of a secondary magnetic source. In the event that a tracer 7 is determined to not be present, it may be more appropriate to use the response signal from $T_{HIGH}$, as this may allow the detection of a marker 6 at a greater distance. In this way, a more accurate detection of a marker 6 that is further away from the probe 10 may be achieved in the absence of a secondary source.

Once a response signal has been selected, the marker 6 may be detected in accordance with the present disclosure using information coming only from selected response signal (e.g. a ratio between harmonic components).

Figure 7:
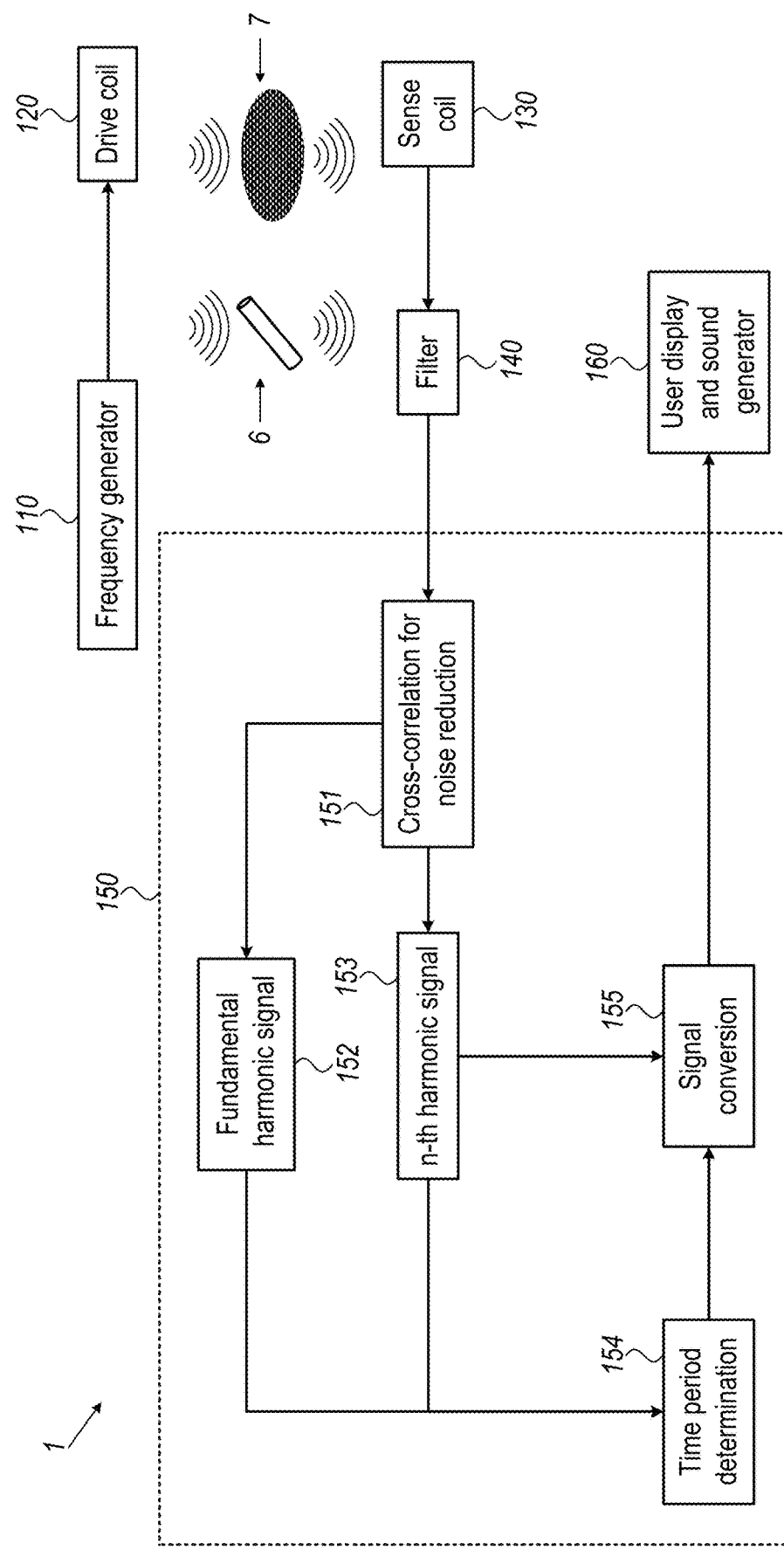
FIG. 7 is a schematic diagram of a magnetic detection system according to an embodiment.

FIG. 7 shows a block diagram of a magnetic detection system 1 according to an embodiment of the present disclosure. The magnetic detection system 1 comprises a frequency generator 110. An oscillator or a waveform generator is a suitable example of a frequency generator 110. The frequency generator 110 is configured to generate an alternating signal in operation. The signal may be sinusoidal. A frequency $f_D$ of the signal may be in a range of 100 Hz to 100 kHz. A suitable example of a frequency generator is a microcontroller outputting a sine wave that is converted to an analogue signal by a digital-to-analogue (DAC) converter, amplified by an analogue amplifier and filtered by a low pass filter to smooth the signal. Alternatively, in some implementations a digital amplifier may be used.

In use, the frequency generator 110 amplifies the signal to one of one or more predetermined amplitude levels. According to an embodiment, the frequency generator 110 may amplify the signal to two or more amplitude levels in a time sequence. For example, the signal amplitude may alternate between a first amplitude level $A_{HIGH}$ and a second amplitude level $A_{LOW}$. The first amplitude level $A_{HIGH}$ may be larger than the second amplitude level $A_{LOW}$. A ratio of the first amplitude level $A_{HIGH}$ to the second amplitude level $A_{LOW}$ may be in the range of 1 to 10. For example, the ratio between amplitude levels may be 2. Advantageously, in accordance with the present disclosure, both $A_{HIGH}$ and $A_{LOW}$ are non-zero, as described below.

The frequency generator 110 may output the signal at the first amplitude level $A_{HIGH}$ for a first time period $T_{HIGH}$ and output the second amplitude level $A_{LOW}$ for a second time period $T_{LOW}$. In an implementation, the first time period $T_{HIGH}$ and the second time period $T_{LOW}$ may be substantially equal in length. Alternatively, in some implementations, the time periods may be different in length. A ratio between $T_{HIGH}$ and $T_{LOW}$ may be referred to as a duty cycle of the signal. The duty cycle may be expressed as a percentage of the total cycle that is the first time period $T_{HIGH}$. The duty cycle may be, for example, about 25%, 50% or 75%, or may be any other suitable value. The total period of time $T_{HIGH}$+$T_{LOW}$ may be 100 ms or less in order that the overall refresh cycle time for the signal to the user can be maintained at a frequency of at least 10 Hz without a significant lag in the output signal versus the changing magnetic response.

In operation, the signal amplitude may alternate continually between the first amplitude level $A_{HIGH}$ and the second amplitude level $A_{LOW}$ without interruption. In some embodiments, the signal may cycle through more than two successive non-zero amplitudes which are different from one another to allow discrimination between the marker 6 and the tracer 7 or other background magnetic sources, as described herein. However, the signal may advantageously never be interrupted while the system is operating; that is, the signal may never have an amplitude of zero. This may be important because the system of the present disclosure is used to detect subtle changes of magnetic field. Repeatedly applying a voltage to the probe 10 with periods of no signal in between may lead to significant inaccuracies in detecting the marker 6 as a result of thermal drift, resulting from significant repeated thermal expansion and retraction of the materials. Even a slight change caused by thermal expansion/retraction of the probe 10 may have a dramatic effect on the accuracy of the detection. By using two amplitudes, one after the other without interruption according to the present disclosure, such a thermal effect may be minimised.

The generated signal excites one or more drive coils 120. The one or more drive coils generate an alternating magnetic field. The generated field extends into tissue containing a magnetic marker 6 comprising at least one piece of a large Barkhausen jump material (LBJ). As described herein, the alternating magnetic field may be generated at two or more different amplitude levels corresponding to the respective amplitude levels of the driving signal. For example, the magnetic field may be generated at a first amplitude level $H_{HIGH}$ and a second amplitude level $H_{LOW}$ corresponding respectively to the amplitude levels $A_{HIGH}$ and $A_{LOW}$.

The driving signal generated by the frequency generator 110 may be electronically filtered to attenuate any harmonic parts of the drive signal so that the alternating magnetic field is primarily or substantially at the desired excitation or drive frequency. Filtering and processing of the driving signal may significantly reduce any harmonic frequency component by several orders of magnitude. This may help to avoid spurious responses at higher frequencies that could be erroneously interpreted as harmonic responses.

The alternating magnetic field excites the marker 6. Magnetisation of the marker 6 leads to the generation of harmonic components in the response field, as described above. Depending on the arrangement of the marker 6, the harmonics may be odd harmonics, (3rd, 5th, 7th etc.) or even harmonics (2nd, 4th, 6th etc.) or a combination of odd and even harmonics. The marker 6 may be detected by measuring the magnitude of one or more of the harmonic frequencies directly or by measuring a ratio of the magnitude of one or more harmonics to the magnitude of one or more other harmonics, or to the magnitude of the fundamental frequency, within the sensed signal.

The alternating magnetic field may also excite the tracer 7. The tracer distribution in space is normally unknown. If the amplitude of the alternating magnetic field is below the above-mentioned linear threshold for all of the tracer 7 in a volume surrounding the probe 10 then a magnetic response of the tracer 7 is linear, independent of the distribution of the tracer in space. Magnetisation of the tracer leads to the generation of a response field with a large fundamental frequency component, in response to the driving magnetic field at the fundamental frequency.

However, if the amplitude of the alternating magnetic field is above the linear threshold for any of the tracer 7 in the volume surrounding the probe 10 then a magnetic response of the tracer 7 may be non-linear. A non-linear response of the tracer 7 may lead to one or more higher frequency components in response to the driving magnetic field. Thus, the response field generated by the tracer 7 may include one or more harmonic frequency components, in response to the driving magnetic field at the fundamental frequency.

The response field from the marker 6 and the tracer 7 is detected by one or more sense coils 130 to generate a sense voltage or current. For example, the sense coils 130 may determine a first sensed signal $S_1$ during the first time period $T_{HIGH}$ and a second sensed signal $S_2$ during the second time period $T_{LOW}$ as described above. Further sensed signals $S_n$ may be detected during further time periods if the driving signal comprises more than two different amplitudes. The sense coils 130 may be arranged in a handheld or robotic probe, such for example as the probe 10. An electronic filter 140 may be arranged to attenuate at least components of the successive sensed signals at the drive frequency so that the resulting signals have minimal content at the drive frequency and comprise higher harmonic components of the signals; for example the second, third, fourth, fifth or seventh order harmonics or permutations or combinations of these. The filter 140 may take the form of a passive LCR type filter comprising a known arrangement of, for example, capacitors, inductors and resistors, or an active filter comprising a known arrangement; for example an arrangement based on one or more op-amps.

The filtered signals may be fed to a harmonic detection circuit 150 as shown in FIG. 7, which improves the signal to noise ratio of one or more harmonic components of the sensed signals S1, S2, Sn and converts the signals to a measure of distance from the probe 10 to the marker 6. The harmonic detection circuit 150 may be configured to filter a spurious harmonic response generated by the tracer 7 or other background magnetic material. The harmonic detection circuit 150 may perform a number of operational steps. The functions of the harmonic detection circuit 150 may be performed by a microcontroller and FPGA, as described above.

The harmonic detection circuit 150 may be configured to perform cross-correlation for noise reduction 151. The harmonic detection circuit 150 may be configured to separate the successive sensed signals S1, S2, Sn into a plurality of frequency components by cross-correlation 151. For example, the cross correlation 151 may separate each of the signals into a fundamental harmonic signal 152 and at least one n-th harmonic signal 153.

The harmonic detection circuit 150 may be configured to perform a time period determination 154. The time period determination includes determining whether to use the first time period $T_{HIGH}$ or the second time period $T_{LOW}$ for localisation of the marker 6. For example, where two different amplitudes $A_{HIGH}$, $A_{LOW}$ are employed, time period determination 154 may be based on a spectral analysis of the first sensed signal $S_1$ and the second sensed signal $S_2$. The analysed spectra may be compared with predetermined values, e.g., known or expected values corresponding to the sensed signals. For example, the first sensed signal $S_1$ and/or the second sensed signal $S_2$ may be compared with pre-recorded responses from an isolated magnetic marker and an isolated secondary source.

The time period determination 154 may be based on the fundamental harmonic signal 152 and at least one n-th harmonic signal 153 generated for each of the sensed signals $S_1$ and $S_2$. For example, a ratio between the fundamental harmonic signal 152 and at least one n-th harmonic signal 153 may be calculated for each of the sensed signals $S_1$ and $S_2$. The ratio may be referred to as a harmonic ratio. The harmonic detection circuit 150 may be configured to calculate a first harmonic ratio $R_1$ based on the fundamental harmonic signal 152 and an n-th harmonic signal 153 in the first sensed signal $S_1$. The harmonic detection circuit 150 may be configured to calculate a second harmonic ratio $R_2$ based on the fundamental harmonic signal 152 and an n-th harmonic signal 153 in the second sensed signal $S_2$. In other embodiments, the time period determination 154 may be based on two or more harmonic signals other than the fundamental harmonic signal, which are generated for each of the sensed signals $S_1$ and $S_2$. For example, a ratio between the n-th harmonic signal 153 and a further (n+x)-th harmonic signal (not shown), where x is an integer, e.g. an odd integer or an even integer, may be calculated for each of the sensed signals $S_1$ and $S_2$.

In some examples, the time period determination 154 may be based on a comparison of $R_1$ and $R_2$. It may be determined that the response of the first sensed signal $S_1$ is more linear than expected. For example, it may be determined that $R_1$ is substantially higher than $R_2$. This may indicate that, from the magnetic material that has been excited, a greater amount than expected is generating a fundamental harmonic signal 152 without generating an n-th harmonic signal 153, i.e. more than expected of the excited magnetic material comprises non-LBJ material. This may be an indication of the presence of a secondary source in the vicinity of the probe 10, where the secondary source is more linear than the marker 6. For example, this may indicate that a tracer 7 is present.

Based on the determined presence of a tracer 7, the time period determination 154 may determine that the second time period $T_{LOW}$ is more appropriate for detecting the proximity of the marker 6.

In some examples, the time period determination 154 may be based on a threshold value for $R_1$. For example, a threshold may be based on an expected response for the marker 6. A marker 6 may typically have a designed or measured response ratio between the fundamental harmonic signal 152 and an n-th harmonic signal 153. For example, a particular marker 6 may have a ratio in the range of 100 to 5000 or, more specifically, a ratio of approximately 400 between, e.g., the fundamental harmonic signal 152 and, say, a 3rd harmonic signal. A threshold value for $R_1$ may be set to be higher than this ratio, e.g. higher than 400. A value of $R_1$ for a sensed signal that is greater than the threshold may indicate the presence of more non-LBJ material than would be expected for the marker 6 alone, indicating the presence of a tracer 7 or other secondary source of magnetic material.

In some cases, as discussed, the tracer 7 may exhibit a non-linear response during the first time period $T_{HIGH}$. A non-linear response of the tracer 7 may be more linear than the response of the marker 6. In such cases, it may be possible to determine the presence of the tracer 7 based on a change in linearity between the first and second time periods $T_{HIGH}$ and $T_{LOW}$.

In some examples, a time period determination 154 may be based on the second sensed signal $S_2$. The ratio $R_2$ may be more linear than expected for the marker 6 alone. For example, $R_2$ may be greater than the expected ratio for a marker 6. A threshold may be set for $R_2$. A value of $R_2$ above the threshold may indicate the presence of a tracer 7.

In some examples, a minimum threshold may be applied to the n-th harmonic signal 153 for either or both of the sensed signals $S_1$ and $S_2$. In this way, false switching can be avoided. For example, if the absence of a marker 6 leads to an n-th harmonic signal 153 that is zero or is at the level of background noise, then the ratio $R_1$ or $R_2$ may be unrealistically high.

If it is determined that a secondary source is present, for example, a tracer 7 is present, then the marker 6 may be located using the second sensed signal $S_2$ only. During the first time period $T_{HIGH}$, the n-th harmonic signal 153 may include a component from a non-linear response of the tracer 7. It may not be appropriate to use the first sensed signal $S_1$ from the first time period $T_{HIGH}$. The response of the tracer 7 in the second time period $T_{LOW}$ may be assumed to be linear. The fundamental harmonic signal 152 may be disregarded and the marker 6 may be located using the n-th harmonic signal 153 from the second sensed signal $S_2$.

If it is determined that a secondary source is not present, for example, a tracer 7 is not present, then the marker 6 may be located using the first sensed signal $S_1$ and/or the second sensed signal $S_2$. The time period determination 154 may determine that the first time period $T_{HIGH}$ is more appropriate, thereby to increase the detection range for the marker 6 using the greater field strength $H_{HIGH}$.

In some embodiments, a second determination is made in this case. If the second sensed signal $S_2$ is particularly high, it may be an indication that the marker 6 is in very close proximity to the probe 10. The time period determination 154 may determine that the second time period $T_{LOW}$ is more appropriate. In particular, the second sensed signal $S_2$ only may be used because the marker 6 may show anomalous behaviour at high driving fields during the first time period $T_{HIGH}$. In some examples, the time period determination 154 may determine that using both the first time period $T_{HIGH}$ and the second time period $T_{LOW}$ is appropriate.

A similar methodology can be applied to reject spurious signals arising from different sources, other than a tracer 7. For example, a linear signal could originate from metal objects that are in the proximity of the probe 10 during surgery; from the patient's body, from the surgeon's hands or from a biopsy marker. The harmonic detection circuit 150 may reject any such signals that are small enough that they do not saturate electronic components in the sense circuits.

The harmonic detection circuit 150 may be further configured to perform a signal conversion 155 on the n-th harmonic marker signal 154 to generate an output signal. The output signal may comprise, for example, a marker proximity value, which represents a measure of distance from the probe 10 to the marker 6. The marker proximity signal may be as disclosed by copending International application no. PCT/GB2021/051750.

Thus, the output signal may comprise an audio signal and/or a display signal. A user display and sound generator 160 may provide a visual and/or audio output to the user indicating, for example, the proximity of the marker 6 or the magnitude of the magnetic signal. The system may indicate the proximity, size, distance/direction or orientation of the marker 6, or combinations of these. In some embodiments, the system may further indicate whether or not a secondary source is present, based on the determination of the harmonic detection circuit 150. In some embodiments, the output signal may comprise a haptic signal. By selecting the more or most appropriate driving signal amplitude, and ensuring that the n-th harmonic frequency response is generated only by the marker 6, the magnetic detection system 1 of the present disclosure may provide a significantly improved indication of the proximity, size etc. of the marker 6. In some embodiments, the magnetic detection system 1 may accurately distinguish between a marker 6 and a tracer 7, in order to provide an improved localisation of the marker 6 in the presence of the tracer 7. In some cases, the magnetic detection system 1 may more accurately detect a marker 6 at a greater range in the absence of a tracer 7. The magnetic detection system 1 of the present disclosure may improve the accuracy of localising a marker 6, and allow for a more accurate removal of a corresponding lesion. The magnetic detection system 1 of the present disclosure may thus reduce the occurrence of excess tissue removal, by allowing a surgeon to determine more accurately the extent of a lesion, thus improving recovery time and a better surgical outcome.

In other cases, the magnetic detection system 1 of the present disclosure may provide a more accurate indication of the size or quantity of a magnetic marker, where the magnetic marker may correspond to a sample of any material providing a non-linear magnetic response. The magnetic detection system 1 of the present disclosure may improve the determination of size or quantity, even when the drive signal includes a spurious frequency component in addition to the desired fundamental frequency component.

In some embodiments, the system of the present disclosure may output an indication that a secondary source is present, without making a determination to use the second sensed signal $S_2$ only. For example, it may not be possible to perform the above described correction, e.g., owing to unduly high secondary signals. In such cases, the system is able to provide an indication to the user that a secondary source may be causing interference.

The markers for use with the detection system of the the present disclosure as described herein may each comprise one or more lengths of material ("magnetic marker material") which give a harmonic or non-linear response to an alternating magnetic field produced by a large Barkhausen discontinuity in their magnetisation curves. Examples of such materials include iron-, cobalt- and nickel-rich glass-coated amorphous microwires, iron-silicon-boron based amorphous microwires, iron-cobalt based amorphous microwires, and bulk metallic glass wires.

In some embodiments, the length or lengths of magnetic marker material (formed from a material with a large Barkhausen discontinuity in its magnetisation curve) may comprise a length of solid wire (<10 mm long) with a diameter <2 mm so that the marker can be delivered through a small needle; a glass-coated microwire with core diameter between, e.g., 5 and 100 micrometres, and a coating thickness of between, e.g., 0.5 and 40 micrometres; a bundle of two or more lengths of solid wire or glass-coated microwire; or a hollow tube.

Any of the markers may comprise more than one piece of magnetic marker material together with additional material to join or enclose the pieces of magnetic marker material and form the final outer shape of the marker. The marker may comprise a tube, tubes or a complete or partial shell of another material within which the lengths of magnetic material of the marker are held. The marker may comprise electronic components e.g. coils, diodes and transistors; for example an LC circuit (a combination of a capacitor and an inductor) with a diode may produce a non-linear response. The magnetic material may be coated or enclosed within a biocompatible material. For example, the tube or shell containing the magnetic marker material may comprise a biocompatible, plastically deformable material such as a 316 stainless steel, Titanium, Nitinol, Titanium alloy or similar.

In some embodiments, the probe 10 may comprise one or more drive coils 120. Alternatively, an alternating magnetic field may be generated by, for example, a spinning permanent magnet.

The probe 10 may comprise one or more sense coils 130 or, alternatively, a solid state magnetometer. In some implementations, the probe 10 may comprise any suitable magnetic sensor, e.g., a Hall effect sensor, mems sensor, magneto-transistor/magneto-diode, a SQUID magnetometer, AMR (Anisotropic Magneto-Resistive) sensor, or a GMR (Giant Magneto Resistance) sensor.

The driving frequency may be in the range 100 Hz to 100 kHz. Higher frequencies towards 100 kHz may be advantageous to maximise the sensed signal. A higher frequency may also allow more cycles per second to be averaged during detection to improve noise suppression while still delivering a 'real time' output to the user, i.e. updating the output signal at least 10 times per second. Hence for noise suppression a frequency of at least 1000 Hz and preferably at least 10 kHz may be desirable. For example, in order to give an apparent 'real time' response to the user, the output may need to update at least every 0.1 s. A frequency of 1 kHz allows 100 cycles to be averaged between each update to the user, and 10 kHz allows 1000 cycles to be averaged between each update to the user.

Advantages may also be gained from a lower drive frequency, and these include reduced eddy current losses both in the marker (in cases where it is prone to eddy currents; for example if it has high conductivity) and from the surrounding tissue and more intense magnetic switching in the marker. For reduced eddy current losses, a frequency of less than 50 kHz and preferably less than 30 kHz may be advantageous. In an operating room environment, electromagnetic interference signals may be more frequently experienced at frequencies above 100 kHz and therefore choosing a drive frequency such that the harmonics of interest are less than 100 kHz may be beneficial.

Although aspects of the present disclosure have been described with reference to particular embodiments, it is to be understood that these embodiments are merely illustrative of the principles and applications of the disclosure. It is therefore to be understood that numerous modifications may be made to the illustrative embodiments and that other arrangements may be devised without departing from the scope of the disclosure as defined by the appended claims.

While various details have been set forth in the foregoing description, it will be appreciated that the various aspects of the techniques for operating a diagnostic and/or surgical guidance system suitable for identifying, localizing, tracking, and detecting position of one or more implanted markers may be practised without these specific details. One skilled in the art will recognize that the herein described components (e.g., operations), devices, objects, and the discussion accompanying them are used as examples for the sake of conceptual clarity and that various configuration modifications are contemplated. Consequently, as used herein, the specific exemplars set forth and the accompanying discussion are intended to be representative of their more general classes. In general, use of any specific exemplar is intended to be representative of its class, and the non-inclusion of specific components (e.g., operations), devices, and objects should not be taken limiting.

Further, while several forms have been illustrated and described, it is not the intention of the applicant to restrict or limit the scope of the appended claims to such detail. Numerous modifications, variations, changes, substitutions, combinations, and equivalents to those forms may be implemented and will occur to those skilled in the art without departing from the scope of the present disclosure. Moreover, the structure of each element associated with the described forms can be alternatively described as a means for providing the function performed by the element. Also, where materials are disclosed for certain components, other materials may be used. It is therefore to be understood that the foregoing description and the appended claims are intended to cover all such modifications, combinations, and variations as falling within the scope of the disclosed forms. The appended claims are intended to cover all such modifications, variations, changes, substitutions, modifications, and equivalents.

For conciseness and clarity of disclosure, selected aspects of the foregoing disclosure have been shown in block diagram form rather than in detail. Some portions of the detailed descriptions provided herein may be presented in terms of instructions that operate on data that is stored in one or more computer memories or one or more data storage devices of the base station or the one or more processors or microprocessors operative therein (e.g. floppy disk, hard disk drive, caches, random access memory, and other optical and magnetic storage devices and media). Such descriptions and representations are used by those skilled in the art to describe and convey the substance of their work to others skilled in the art. In general, an algorithm refers to a self-consistent sequence of steps leading to a desired result, where a "step" refers to a manipulation of physical quantities and/or logic states which may, though need not necessarily, take the form of electrical or magnetic signals capable of being stored, transferred, combined, compared, and otherwise manipulated. It is common usage to refer to these signals as bits, values, elements, symbols, characters, terms, numbers, or the like. These and similar terms may be associated with the appropriate physical quantities and are merely convenient labels applied to these quantities and/or states. The various methods steps disclosed herein may be implemented or programmed as algorithms, data structures, and instructions that may operate upon inputs from data channels and generate outputs that contain various types of data such as user actional data, user feedback signals, information, and images.

Unless specifically stated otherwise as apparent from the foregoing disclosure, it is appreciated that, throughout the foregoing disclosure, discussions using terms such as "processing" or "computing" or "calculating" or "determining" or "displaying" or the like, refer to the action and processes of a computer system, processor-based base station, or similar electronic computing device, that manipulates and transforms data represented as physical (electronic) quantities within the computer system's registers and memories into other data similarly represented as physical quantities within the computer system memories or registers or other such information storage, transmission or display devices.

In a general sense, those skilled in the art will recognize that the various aspects described herein which can be implemented, individually and/or collectively, by a wide range of hardware, software, firmware, or any combination thereof can be viewed as being composed of various types of "electrical circuitry." Consequently, as used herein "electrical circuitry" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), and/or electrical circuitry forming a communications device (e.g., a modem, communications switch, or optical-electrical equipment). Those having skill in the art will recognize that the subject matter described herein may be implemented in an analogue or digital fashion or some combination thereof.

The foregoing detailed description has set forth various forms of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, and/or examples can be implemented, individually and/or collectively, by a wide range of hardware, software, firmware, or virtually any combination thereof. In one form, several portions of the subject matter described herein may be implemented via an application specific integrated circuits (ASIC), a field programmable gate array (FPGA), a digital signal processor (DSP), or other integrated formats. However, those skilled in the art will recognize that some aspects of the forms disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure.

In addition, those skilled in the art will appreciate that the mechanisms of the subject matter described herein are capable of being distributed as one or more program products in a variety of forms, and that an illustrative form of the subject matter described herein applies regardless of the particular type of signal bearing medium used to actually carry out the distribution. Examples of a signal bearing medium include, but are not limited to, the following: a recordable type medium such as a floppy disk, a hard disk drive, a Compact Disc (CD), a Digital Video Disk (DVD), a digital tape, a computer memory, etc.; and a transmission type medium such as a digital and/or an analogue communication medium (e.g., a fibre optic cable, a waveguide, a wired communications link, a wireless communication link (e.g., transmitter, receiver, transmission logic, reception logic, etc.), etc.).

Also, as described, some aspects may be embodied as one or more methods. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

The phrase "and/or," as used herein in the specification and in the claims, should be understood to mean "either or both" of the elements so conjoined, i.e., elements that are conjunctively present in some cases and disjunctively present in other cases.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified.

The terms "approximately" and "about" may be used to mean within +20% of a target value in some embodiments, within ±10% of a target value in some embodiments, within +5% of a target value in some embodiments, and yet within +2% of a target value in some embodiments. The terms "approximately" and "about" may include the target value.

In the claims, as well as in the specification above, all transitional phrases such as "comprising," "including," "carrying," "having," "containing," "involving," "holding," "composed of," and the like are to be understood to be open-ended, i.e., to mean including but not limited to. The transitional phrases "consisting of" and "consisting essentially of" shall be closed or semi-closed transitional phrases, respectively.

Where a range or list of values is provided, each intervening value between the upper and lower limits of that range or list of values is individually contemplated and is encompassed within the disclosure as if each value were specifically enumerated herein. In addition, smaller ranges between and including the upper and lower limits of a given range are contemplated and encompassed within the disclosure. The listing of exemplary values or ranges is not a disclaimer of other values or ranges between and including the upper and lower limits of a given range.

The use of headings and sections in the application is not meant to limit the disclosure; each section can apply to any aspect, embodiment, or feature of the disclosure. Only those claims which use the words "means for" are intended to be interpreted under 35 USC 112, sixth paragraph, and even then only in the United States. Absent a recital of "means for" in the claims, such claims should not be construed under 35 USC 112. Outside the United States, the words "means for" are intended to have their natural meaning. Limitations from the specification are not intended to be read into any claims, unless such limitations are expressly included in the claims.

Embodiments disclosed herein may be embodied as a system, method or computer program product. Accordingly, embodiments may take the form of an entirely hardware embodiment, an entirely software embodiment (including firmware, resident software, micro-code, etc.) or an embodiment combining software and hardware aspects that may all generally be referred to herein as a "circuit," "module," or "system." Furthermore, embodiments may take the form of a computer program product embodied in one or more computer readable medium(s) having computer readable program code embodied thereon.

Although aspects of the invention herein have been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the scope of the invention as defined by the appended claims.

The invention claimed is:

1. A method for detecting a magnetic marker, the method comprising generating a driving magnetic field having a cyclic pattern comprising two or more successive periods of time, the driving magnetic field having a substantially constant, non-zero amplitude during each of the successive periods of time, and the amplitude of the driving magnetic field during at least one of the periods of time being different from the amplitude of the driving magnetic field during at least one other of the periods of time; detecting a response magnetic field; selecting at least one signal from a plurality of sensed signals, each of which corresponds to the response magnetic field detected during a respective one of the successive periods of time of each cycle; determining a detection signal corresponding to the magnetic marker using the at least one selected signal; and generating an output signal based on a strength of the detection signal.

2. The method of claim 1, wherein the two or more successive periods of time forming the cyclic pattern are substantially contiguous to one another.

3. The method of claim 1, wherein the amplitude of the driving magnetic field during at least one of the successive periods of time is high in relation to the amplitude of the driving magnetic field during at least one other of the successive periods of time.

4. The method of claim 1, wherein the amplitude of the driving magnetic field during at least one other of the successive periods of time is relatively low in comparison to the amplitude of the driving magnetic field during at least one of the successive periods of time.

5. The method of claim 1, wherein the response magnetic field is detected across substantially the whole of the repeating pattern of successive time periods.

6. The method of claim 1, wherein the duration of the successive periods of time within each cycle is substantially the same.

7. The method of claim 1, wherein the driving magnetic field has a substantially constant frequency during all of the successive periods of time.

8. The method of claim 1, wherein the cyclic pattern comprises two successive periods of time, and the response magnetic field comprises a first response component at a first frequency and a second response component at a second frequency which is different from the first frequency.

9. The method of claim 1, wherein the duration of the successive periods of time within each cycle is substantially different from one another.

10. A method for detecting a magnetic marker, comprising:
generating a driving magnetic field comprising a first frequency, the driving magnetic field having a first amplitude for a first period of time and a second amplitude, lower than the first amplitude, for a second period of time, the driving magnetic field alternating between the first amplitude and the second amplitude according to a predetermined duty cycle;
detecting a response magnetic field comprising a first response component at the first frequency and a second response component at a second frequency which is different from the first frequency;

selecting, by a processor based on the response magnetic field, at least one signal from a first sensed signal corresponding to the response magnetic field detected during the first time period and a second sensed signal corresponding to the response magnetic field detected during the second time period;

determining, by the processor, a detection signal corresponding to the magnetic marker using the at least one selected signal; and generating, by the processor for output, an output signal based on a strength of the detection signal.

11. The method of claim 10, wherein a first period of time and a second period of time of the two successive periods of time are shorter than one second.

12. The method of claim 11, wherein identifying the presence of the secondary magnetic source comprises comparing a first harmonic ratio based on the first sensed signal and a second harmonic ratio based on the second sensed signal.

13. The method of claim 11, wherein identifying the presence of a secondary magnetic source is based on comparing a spectral analysis of the response magnetic field with pre-recorded responses from an isolated magnetic marker and an isolated secondary source.

14. The method of claim 10, wherein selecting the at least one signal is based on an absolute magnitude of the first sensed signal and/or the second sensed signal.

15. The method of claim 10, wherein selecting the at least one signal is based on whether the absolute magnitude of the first sensed signal and/or the second sensed signal exceeds a predetermined threshold.

16. The method of claim 10, wherein selecting the at least one signal is based on identifying the presence of a secondary magnetic source.

17. The method of claim 16, wherein the secondary magnetic source is a liquid magnetic tracer.

18. The method of claim 16, wherein identifying the presence of the secondary magnetic source comprises calculating a harmonic ratio between the first response component at the first frequency and the second response component at the second frequency.

19. A magnetic detection system for detecting a magnetic marker for guiding a surgeon to a region of interest during a surgical procedure, the magnetic detection system comprising:

a driving unit configured to generate a driving magnetic field based on a corresponding driving signal which has a cyclic pattern comprising two or more successive periods of time in which the driving signal has a substantially constant, non-zero amplitude during each of the successive periods of time, and the amplitude of the driving signal during at least one of the periods of time is different from the amplitude of the driving signal during at least one other of the periods of time;

a magnetic field sensor configured to detect a response magnetic field;

a processor configured to select, based on the response magnetic field, at least one signal from a plurality of sensed signals, each of which corresponds to the response magnetic field detected during a respective one of the successive periods of time of each cycle; determine a detection signal corresponding to the magnetic marker using the at least one selected signal; and generate an output signal based on a strength of the detection signal.

* * * * *